(12) United States Patent
Wilson et al.

(10) Patent No.: US 11,696,903 B2
(45) Date of Patent: Jul. 11, 2023

(54) COMPOUNDS AND METHODS FOR SCAVENGING DICARBONYL ELECTROPHILES

(71) Applicant: VANDERBILT UNIVERSITY, Nashville, TN (US)

(72) Inventors: Keith T. Wilson, Nashville, TN (US); John A. Oates, Nashville, TN (US); Olivier Boutaud, Nashville, TN (US); Venkataraman Amarnath, Nashville, TN (US); Erica J. Carrier, Nashville, TN (US); Alain P. Gobert, Nashville, TN (US)

(73) Assignees: Vanderbilt University, Nashville, TN (US); The United States as Represented by the Department of Veterans Affairs, Washington, DC (US)

( * ) Notice: Subject to any disclaimer, the term of this patent is extended or adjusted under 35 U.S.C. 154(b) by 143 days.

(21) Appl. No.: 16/893,425

(22) Filed: Jun. 4, 2020

(65) Prior Publication Data

US 2020/0383938 A1 Dec. 10, 2020

Related U.S. Application Data

(60) Provisional application No. 62/857,165, filed on Jun. 4, 2019, provisional application No. 62/978,183, filed on Feb. 18, 2020.

(51) Int. Cl.
*A61K 31/137* (2006.01)
*A61P 31/04* (2006.01)
*A61P 35/00* (2006.01)

(52) U.S. Cl.
CPC ............ *A61K 31/137* (2013.01); *A61P 31/04* (2018.01); *A61P 35/00* (2018.01)

(58) Field of Classification Search
None
See application file for complete search history.

(56) References Cited

U.S. PATENT DOCUMENTS

2015/0265584 A1* 9/2015 Oates .................. A61K 45/06
514/567

OTHER PUBLICATIONS

Li et al., European Journal of Medicinal Chemistry (2009), 44, pp. 2246-2251.*

* cited by examiner

*Primary Examiner* — Brian J Davis
(74) *Attorney, Agent, or Firm* — Stites & Harbison PLLC; Richard S. Myers, Jr.

(57) ABSTRACT

Compounds and methods of scavenging bifunctional electrophiles and reducing the occurrence of lysyl-levuglandin adducts in a subject in need thereof by administering a levuglandin adduct formation inhibiting amount of a compound of the following formula:

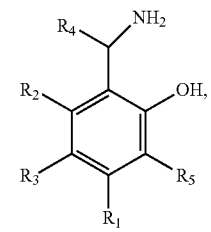

wherein the variables are defined herein.

19 Claims, 12 Drawing Sheets

COMPOUNDS AND METHODS FOR SCAVENGING DICARBONYL ELECTROPHILES

PRIOR APPLICATIONS

This application claims benefit to U.S. Patent Application No. 62/857,165, filed Jun. 4, 2019; and U.S. Patent Application No. 62/978,183, filed Feb. 18, 2020. The contents of both applications are incorporated herein by reference.

GOVERNMENT INTEREST

This invention was made with government support under P30ES000267, P50CA090949, R21CA201856, P01CA028842, P01CA116087, R01CA190612, R01DK053620, P30DK058404, P50GM015431 and 6R21CA187495 awarded by the National Institutes of Health and grant number W81XWH-18-1-0301 awarded by the Department of Defense. The government has certain rights in the invention.

FIELD OF THE INVENTION

Embodiments of this invention relate to methods of inhibiting the modification of histones and DNA by levuglandins in a subject in need thereof by administering a compound of the present invention or a pharmaceutically acceptable salt thereof.

Embodiments of this invention also are scavengers of bifunctional electrophiles, including bifunctional electrophiles that are generated in vivo during carcinogenesis.

Embodiments of this invention also relate to inhibiting the formation of levuglandin adducts.

Embodiments of this invention also relate to inhibiting the development of intramucosal carcinomas, as well as reducing the dysplasia that is a carcinoma precursor.

SUMMARY OF THE INVENTION

The burden of colorectal cancer (CRC) in the United States and worldwide is massive, representing the 3rd most common cancer and 2nd most cause of cancer deaths. The etiology of CRC is multifactorial and encompasses genetic factors, environmental exposures, and/or inflammation. Despite many decades of investigation, the molecular process by which healthy colonic epithelial cells transform remains largely undetermined. In patients with inflammatory bowel disease the risk for cancer is especially high, leading to colitis-associated carcinoma (CAC). The strong mucosal immune response that occurs during colitis leads to the generation of effector molecules, including reactive oxygen species and prostaglandins, which are involved in the formation of dicarbonyl electrophiles, such as levuglandins or malondialdehyde. These electrophiles are highly reactive with DNA and lysine residues, notably in histones, thus favoring mutagenesis and somatic genomic abnormalities. However, the role of endogenous electrophiles in colorectal carcinogenesis remains unknown despite the fact that they can be mutagenic. The present inventors have discovered that electrophiles are involved in colon carcinogenesis: 1) The electrophile protein adducts on lysines are elevated in: i) human tissues from ulcerative colitis (UC), UC dypsplasia, and CAC with a progressive increase; ii) colonic tumors of CRC patients; iii) dyplastic tumors of C57BL/6 mice treated with azoxymethane-dextran sulfate sodium (AOM-DSS), a model of CAC, compared to non-tumor areas; iv) dysplastic tumors of mice with colon-specific homozygous deletion of Apc; 2). The present inventors show that compounds of the present invention are potent scavengers that react with dicarbonyl electrophiles, and inhibit adduct formation. One compound of the present invention, 2-hydroxybenzylamine (2-HOBA) is a natural product that has successfully completed Phase I human testing at Vanderbilt and has been shown to protect mice from oxidative damage in models of hypertension and Alzheimer's disease. Another compound of the present invention, 5-ethyl-2-hydroxybenzylamine (EtHOBA) is an analog of HOBA, which can penetrate the nucleus and protect nuclear proteins from electrophilic oxidation. 3) In the AOM-DSS model, treatment of mice with EtHOBA significantly reduces adduct formation, tumor development and dysplasia, while enhancing antitumoral immune response. The present inventors discovered that electrophiles have a key role in colon carcinogenesis via genomic instability, epigenetic dysregulation, and/or suppression of antitumoral immunity, and are key targets for cancer prevention.

Inflammation and subsequent cyclooxygenase-2 (COX-2) activity has long been linked with the development of cancer, although little is known about any epigenetic effects of COX-2. A product of COX-2 activity, levuglandin (LG) quickly forms covalent bonds with nearby primary amines, such as those in lysine, which leads to LG-protein adducts. Here, the present inventors demonstrate that COX-2 activity causes LG-histone adducts in cultured cells and liver tissue, detectable through LC/MS, with the highest incidence in histone H4. Adduction is blocked by a reactive dicarbonyl scavenger, which has no effect on COX-2 activity as measured by $PGE_2$ production. Formation of LG-histone adduct is associated with an increased histone solubility in NaCl, indicating destabilization of the nucleosome structure; this is also reversed with scavenger treatment. These data demonstrate that COX-2 activity can cause histone adduction and loosening of the nucleosome complex, which could lead to altered transcription and contribute to carcinogenesis.

Additionally, *Helicobacter pylori* (Hp) (*H. pylori*) induces an innate immune response in epithelial and myeloid cells that leads to inflammation-associated cancer. The inflammatory effector molecules, such as prostaglandins and reactive oxygen species, can generate the bifunctional electrophiles: levuglandins (LG), malondialdehyde, 4-oxononenal, and acrolein. These molecules form covalent adducts on DNA bases and on lysines (Lys-LG) in histones, thus disrupting DNA/histone interactions and increasing risk for mutations. The present inventors have discovered that compounds of the present invention scavenge said electrophiles, which prevents adduct formation.

Accordingly, embodiments of the present invention include compounds and methods for scavenging bifunctional electrophiles and/or LG-lysine adducts and/or lysyl-LG adducts in a patient in need thereof.

Another embodiment is a method of inhibiting formation of levuglandin adducts of histone and DNA in a subject in need thereof by administering a compound of the present invention or a pharmaceutically acceptable salt thereof.

Another embodiment of the present invention is a method of treating pre-malignant lesions by administering a compound of the present invention or a pharmaceutically acceptable salt thereof.

Another embodiment of the present invention is a method of scavenging levuglandins in nucleus of cells by administering a compound of the present invention or a pharmaceutically acceptable salt thereof.

Another embodiment of the present invention is preventing malignant mutations of pre-cancerous conditions by administering a compound of the present invention or a pharmaceutically acceptable salt thereof.

Another embodiment of the present invention is decreasing a subject's risk of developing cancer by administering a compound of the present invention or a pharmaceutically acceptable salt thereof.

Another embodiment of the present invention is the prevention of cellular transformation to malignancy by administering a compound of the present invention or a pharmaceutically acceptable salt thereof.

Another embodiment of the present invention is a method preventing further mutations in colon, esophagus, breast, lung, pancreas, gastrointestinal cancer, and/or prostate cancers in a subject in need thereof by administering a compound of the present invention or a pharmaceutically acceptable salt thereof.

Another embodiment of the present invention is a method treating and/or preventing a disorder resulting from elevated levels of LG-histone adduct formation and adducts on DNA bases and on lysines (Lys-LG) in histones.

Another embodiment of the present invention is when the disorder resulting from elevated levels of LG-histone adduct formation is neoplasia. In other embodiments, the neoplasia is a brain cancer, a bone cancer, an epithelial cell-derived neoplasia (epithelial carcinoma), a basal cell carcinoma, an adenocarcinoma, a gastrointestinal cancer, a lip cancer, a mouth cancer, an esophageal cancer, a small bowel cancer, a stomach cancer, a colon cancer, a liver cancer, a bladder cancer, a pancreas cancer, an ovary cancer, a cervical cancer, a lung cancer, a breast cancer, a skin cancer, a squamus cell cancer, a basal cell cancer, a prostate cancer, a renal cell carcinoma, a cancerous tumor, a growth, a polyp, an adenomatous polyp, a familial adenomatous polyposis or a fibrosis resulting from radiation therapy.

Another embodiment of the present invention relates to treatment of a disease such as especially pre-malignant lesions of the gastrointestinal tract, colon or esophagus (Barrett's esophagus) or a colon cancer or other malignancies, preferably pre-malignant colon lesions or a colon cancer, in a subject in need thereof. The other malignancies to be treated according to the present invention are preferably selected from the group consisting of breast cancer, lung cancer, ovarian cancer, lymphoma, head and neck cancer and cancer of the esophagus, stomach, bladder, prostrate, uterus and cervix.

Another embodiment of the present invention is a method of inhibiting the progression of a gastrointestinal cancer in a subject, comprising administering to the subject a levuglandin adduct formation inhibiting amount of a compound of the following formula:

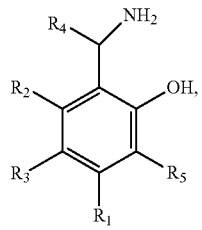

wherein: $R_1$ is H, D, $D_2$, substituted or unsubstituted alkyl, substituted or unsubstituted alkoxy, carboxyl, substituted or unsubstituted aryl, or substituted or unsubstituted cycloalkyl; $R_2$ is H, substituted or unsubstituted alkyl, substituted or unsubstituted alkoxy, alkyl-alkoxy-$R_4$; $R_3$ is H, halogen, substituted or unsubstituted alkyl, substituted or unsubstituted alkoxy, hydroxyl, nitro; $R_4$ H, D, $D_2$, substituted or unsubstituted alkyl, substituted or unsubstituted alkoxy, carboxyl, substituted or unsubstituted aryl, or substituted or unsubstituted cycloalkyl; $R_5$ is H, substituted or unsubstituted alkyl, substituted or unsubstituted alkoxy; and pharmaceutical salts thereof.

In one aspect of this embodiment, the cancer is colorectal cancer.

In another aspect of this embodiment, the compound is 2-hydroxybenzylamine, methyl-2-hydroxybenzylamine, or ethyl-2-hydroxybenzylamine.

Another embodiment of the present invention is a method of mitigating the progression of pre-malignant lesions in a subject in need thereof by administering an effective amount of a compound of the following formula:

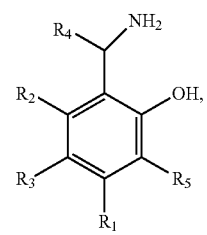

wherein: $R_1$ is H, D, $D_2$, substituted or unsubstituted alkyl, substituted or unsubstituted alkoxy, carboxyl, substituted or unsubstituted aryl, or substituted or unsubstituted cycloalkyl; $R_2$ is H, substituted or unsubstituted alkyl, substituted or unsubstituted alkoxy, alkyl-alkoxy-$R_4$; $R_3$ is H, halogen, substituted or unsubstituted alkyl, substituted or unsubstituted alkoxy, hydroxyl, nitro; $R_4$ H, D, $D_2$, substituted or unsubstituted alkyl, substituted or unsubstituted alkoxy, carboxyl, substituted or unsubstituted aryl, or substituted or unsubstituted cycloalkyl; $R_5$ is H, substituted or unsubstituted alkyl, substituted or unsubstituted alkoxy; and pharmaceutical salts thereof.

In another aspect of this embodiment, the lesions are in a gastrointestinal tract.

Another embodiment of the present invention is a method of treating gastrointestinal carcinoma in a subject in need thereof, comprising administering an *H. pylori* reducing effective amount of a compound of the following formula:

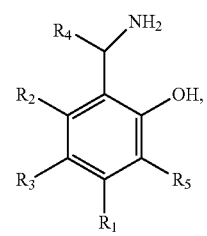

wherein: $R_1$ is H, D, $D_2$, substituted or unsubstituted alkyl, substituted or unsubstituted alkoxy, carboxyl, substituted or unsubstituted aryl, or substituted or unsubstituted cycloalkyl; $R_2$ is H, substituted or unsubstituted alkyl, substituted or unsubstituted alkoxy, alkyl-alkoxy-$R_4$; $R_3$ is H, halogen, substituted or unsubstituted alkyl, substituted or unsubstituted alkoxy, hydroxyl, nitro; $R_4$ H, D, $D_2$, substituted or unsubstituted alkyl, substituted or unsubstituted alkoxy, carboxyl, substituted or unsubstituted aryl, or substituted or unsubstituted cycloalkyl; $R_5$ is H, substituted or unsubstituted alkyl, substituted or unsubstituted alkoxy; and pharmaceutical salts thereof.

In aspects of this embodiment, the lesion exists in the colon, esophagus, breast, lung, pancreas, gastrointestinal tract, and/or prostate.

In other aspects, the inhibition step lowers levels of LG-histone adduct formation in said subject.

In other aspects, the subject was first diagnosed with an *H. pylori* infection.

Another embodiment of the present invention is a commercial package or product comprising an adduction inhibitor, in particular those mentioned herein, or a pharmaceutically acceptable salt thereof, together with instructions for the treatment of a disease such as especially gastrointestinal cancer, pre-malignant gastrointestinal lesions, colon lesions or a colon cancer or other malignancies, preferably pre-malignant colon lesions or a colon cancer, in subject in need thereof.

According to the present invention, a patient is treated with therapeutically effective amounts of an adduction inhibitor of the present invention, each according to a dosage regimen that is appropriate for the individual agent. For example, the adduction inhibitor may be administered once or more daily, on alternate days or on some other schedule—as is appropriate. One of skill in the art has the ability to determine appropriate pharmaceutically effective amounts of the combination components.

In the context of the present invention the terms "treatment" or "treat" refer to both prophylactic or preventative treatment as well as curative or disease modifying treatment, including treatment of patients at risk of contracting the disease or suspected to have contracted the disease as well as patients who are ill or have been diagnosed as suffering from a disease or medical condition.

(B) H&E staining; each arrow depicts a tumor. Lower panel, high power view showing high grade dysplasia. (C) IHC for L G-protein adducts. Scale bar, 50 µm.

Figure 8:
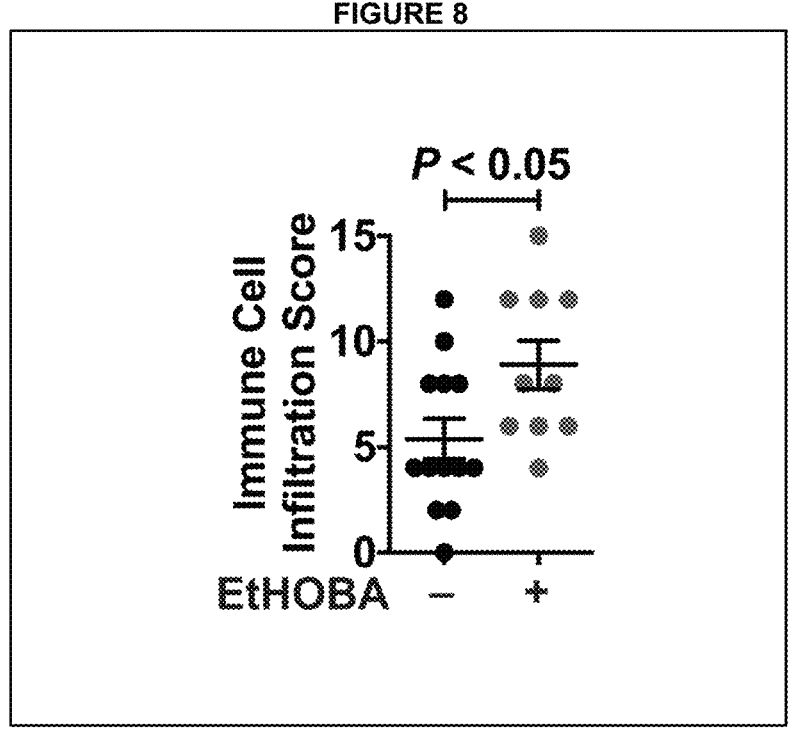

FIG. 8 shows immune cell infiltration score in AOM-DSS-treated mice±EtHOBA.

Figure 9:
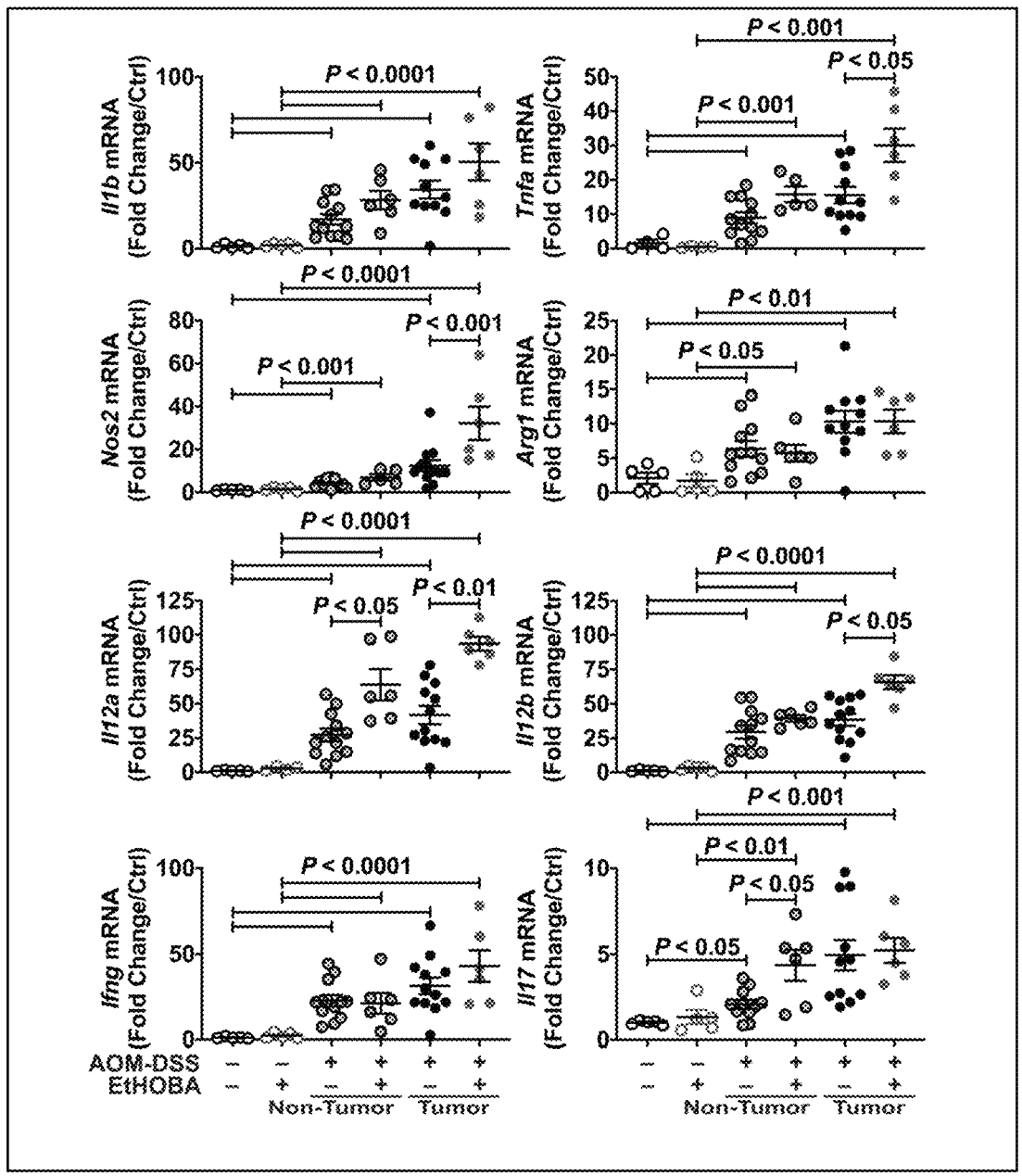

FIG. 9 shows gene expression in the colon tissues of mice treated or not with AOM-DSS±EtHOBA.

Figure 10:
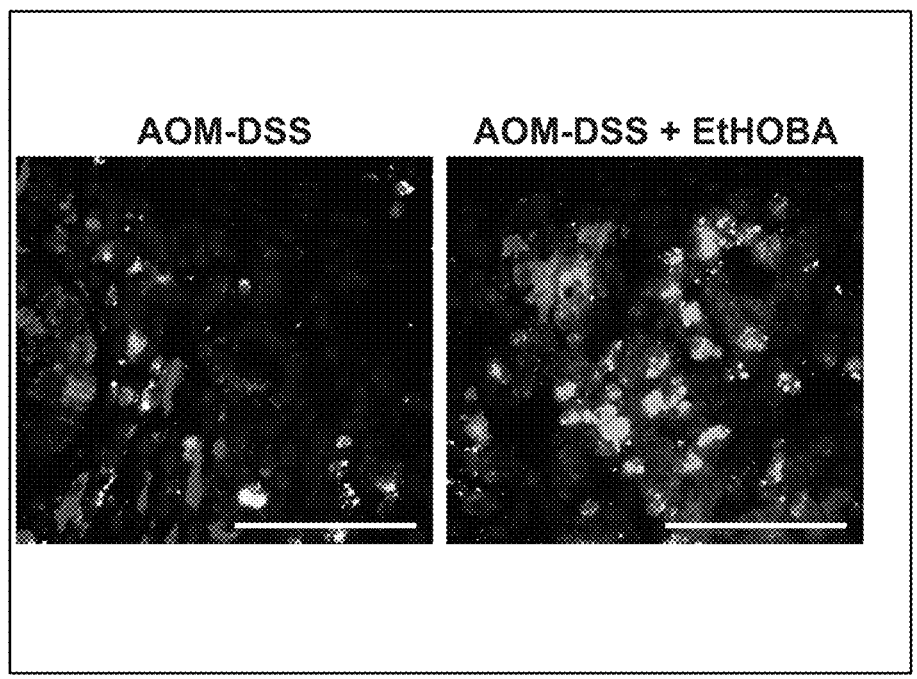

FIG. 10 shows a representative IF for CD68+NOS2+ cells in tumors of AOM-DSS-treated mice±EtHOBA (n=3); NOS2; CD68; DAPI. Scale bar, 50 µm.

FIGS. 11A, 11B, 11C, 11D, 11E, and 11F are a series of graphs showing that LG-lysine adducts of histones are found in cells and tissue, dependent on COX-2 activity. RAW264.7 mouse macrophage (A) and A549 human lung carcinoma (C) cells were stimulated to express COX-2, then given 20 µM arachidonic acid (AA) or vehicle. A subgroup of cells was preincubated 45 min with 50 µM indomethacin. As a measure of COX activity, $PGE_2$ was determined by GC/MS from cell media prior to lysis (B and D). Nuclei were isolated, and histones were extracted and digested to individual amino acids prior to LC/EST/MS/MS analysis. *, p<0.05; ***, p<0.001 by ANOVA followed by Tukey's post-test (n≥5). (E). Histones were extracted from nuclei of rat liver, and analyzed as above for LG-lactam adduct. COX-2 protein was analyzed by Western blotting and plotted against lactam adduct levels. Each point corresponds to 1 liver, and shown is the line of regression ($r^2$=0.7237). Pearson r=0.8507; two-tailed p=0.0152. (F) LC-MS chromatograph of histones isolated from a rat liver with relatively high COX-2 expression (COX-2 band intensity of 117 arbitrary units).

FIGS. 12A, 12B, 12C, 12D show LG-lysyl adducts are predominantly detected on histone H4. (A). A Ponceau stain of a sample A549 histone extraction is shown, along with band identities. Histones were extracted from nuclei in 0.4N $H_2SO_4$, resolved on 4-12% SDS-PAGE gradient gel and transferred to nitrocellulose. H3 and H2B tend to run together as one band. (B). RAW264.7 or A549 cells were stimulated to express COX-2 and given 20 µM $^{14}$C-AA for 1 h. Cells were lysed, nuclei were isolated, and histones extracted, concentrated, and resolved on SDS-PAGE prior to transferring to nitrocellulose and exposing to film. Shown is the Coomassie stain of the SDS-PAGE gel (left) and the result of autoradiography (right). The present inventors have observed that Ponceau, Coomassie, and silver stains each preferentially detect different histone or acid-soluble proteins. (C-D). RAW264.7 (C) or A549 (D) cells were stimulated to express COX-2, and treated with 20 µM AA for 1 h prior to histone extraction. 350-400 µg of total histone was loaded onto 4-12% SDS-PAGE gel and transferred to nitrocellulose. Individual bands were excised horizontally and proteins digested directly off the nitrocellulose by serial incubations with Pronase and aminopeptidase. The results were analyzed by LC/ESI/MS/MS, and the chromatographs of the H3/H2B and H4 bands shown against the LG-lysyl internal standard. The H2A chromatograph is shown as a representative negative result; no co-migrating peaks were seen in any other bands.

Figures 13A, 13B, 13C:
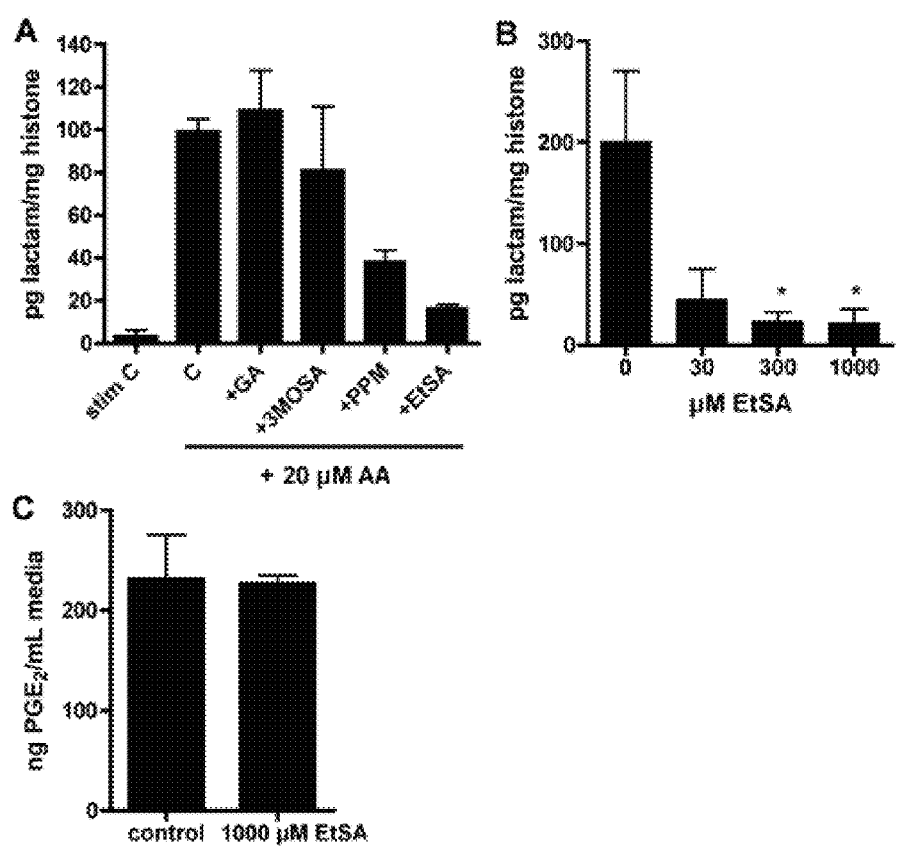

FIGS. 13A, 13B, and 13C show that the scavenger EtSA blocks LG-lysyl adduct formation in RAW264.7 and A549 histones, without affecting COX-2 activity. (A). Scavengers were screened in RAW264.7 cells for the ability to decrease LG adduct formation on histones. Scavengers used were glucosamine (GA), 3-methoxysalicylamine (3-MoSA), pentylpyridoxamine (PPM), and 5-ethylsalicylamine (EtSA). Cells were stimulated to express COX-2, pretreated 45 min. with 500 µM scavenger or vehicle ($H_2O$), and given 20 µM AA for 1 h before lysing and extracting histones. Histone proteins were analyzed by LC/ESI/MS/MS for LG-lysyl lactam adduct, n=2. (B) Stimulated A549 cells were pretreated with 30, 300, or 1000 μM EtSA prior to 1 h with 20 μM AA, and histones analyzed for LG-lysyl adduct. *, $p<0.05$ by one-way ANOVA followed by Dunnett's multiple comparisons post-test (n=3-5). (C). A549 cells were stimulated, pretreated 45 min. with 1000 μM EtSA or H$_2$O vehicle, and given 20 μM AA for 1 h. Media was analyzed by GC/MS for PGE$_2$ (n=3). There was no effect on PGE$_2$ production at lower doses of EtSA (data not shown).

Figures 14A, 14B:
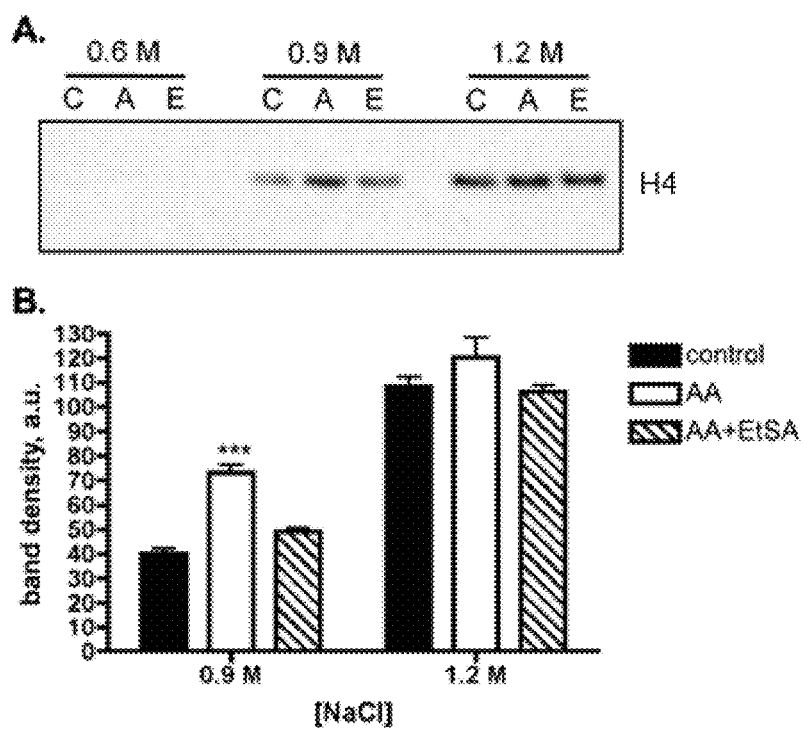

FIG. 14. LG-lysyl adduct formation on histone H4 decreases DNA-histone interaction. A549 cells were stimulated and given DMSO vehicle (C lanes) or 20 μM AA for 1 h (A lanes). A subgroup of cells was treated with 500 μM EtSA 45 min prior to adding AA (E lanes). Nuclei were extracted with 0.6, 0.9, or 1.2 M NaCl buffer, and the supernatant evaluated by Western blotting for histone H4. Shown is a representative Western blot (A) as well as the pooled results of 4 experiments (B). Different exposure times may have been used for the 0.9 M and 1.2 M bands. ***, $p<0.001$ by one-way ANOVA followed by Tukey's multiple comparisons post-test. NS, not significant.

Figures 15A, 15B, 15C:
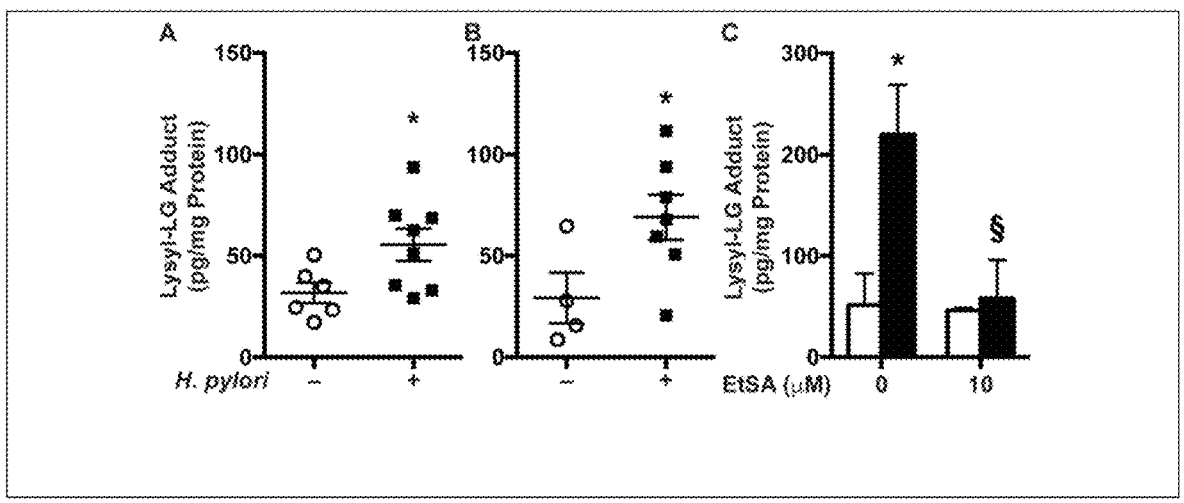

FIGS. 15A, 15B, and 15C are graphs showing C57BL/6 (A) or INS-GAS mice (B) were infected for 8 weeks with *H. pylori* PMSS1. Lysyl-LG adducts were measured in the gastric tissues by LC/ESI/MS/MS. *$P<0.05$. (C) Lysyl-LG adducts concentration was determined in AGS cells infected (plain bars) or not (open bars) with *H. pylori* PMSS1 for 24 h, in the presence or absence of EtSA. *$P<0.05$ vs. uninfected cells. § $P<0.05$ vs. infected cells without EtSA.

FIGS. 16A, 16B, 16C, 16D, 16E, and 16F show INS-GAS mice (8 per group) were infected or not with *H. pylori* strain PMS for 8 weeks and then treated with EtSA (7.5 mg/ml) one week after infection. (A) EtSA concentration in gastric tissues; $P<0.01$, **$P<0.0001$ vs. mice without EtSA. (B) Frequency of diagnoses. IMC, intramucosal carcinoma; LGD, low grade dysplasia; ND, no dysplasia. (C) Quantification of extent of dysplasia and cancer as a percentage of tissue sections. (D) H&E staining of INS-GAS mouse stomach tissues, showing carcinoma in an infected mouse; scale bar, 50 μm. In B and C, *$P<0.05$, **$P<0.01$ vs. infected mice.

Figure 17:
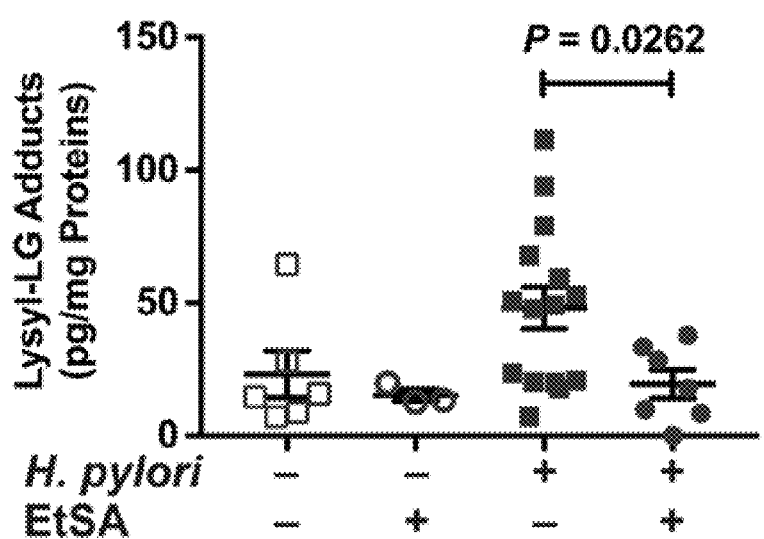

FIG. 17 is a graph showing reduction in the concentration of lysyl-levuglandin adducts in the stomachs of *H. pylori* infected mice treated with 2-hydroxybenzylamine for 8 weeks.

DESCRIPTION OF THE INVENTION

The present invention can be understood more readily by reference to the following detailed description of the invention and the Examples included therein.

Before the present compounds, compositions, articles, systems, devices, and/or methods are further disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which need to be independently confirmed.

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "levuglandin scavenger" is a compound that prevents reactive carbonyls such as levuglandin from reacting with DNA and proteins. Without being bound by theory or mechanism, this may occur by reacting with the carbonyls to form covalent adducts, thus preventing them from forming adducts of DNA and proteins. Examples include covalent adducts on DNA bases and on lysines (Lys-LG) in histones.

One embodiment of the present invention is a method of treating gastrointestinal cancer, including colorectal cancer (CRC). Despite intensive efforts at colonoscopy-based screening, the disease burden of CRC remains vast; it has the third highest incidence and the second highest mortality rate of all cancers. While there has been great interest in chemoprevention strategies, e.g. aspirin2, COX2 inhibitors, difluoromethylornithine+sulindac4, there is no effective strategy that has impacted on clinical practice. Further, despite many studies of oncogene and tumor suppressor gene alterations, the exact molecular mechanisms by which malignant lesions occur in the epithelium remain unclear. There are high-risk populations, including patients with: 1) longstanding inflammatory bowel disease (IBD), and 2) history of high-risk adenomas or genetic abnormalities (e.g. familial adenomatous polyposis coli; FAP) that are strong candidates for chemoprevention.

Under conditions such as inflammation and/or accumulated mutations, epithelial cells and adjacent immune cells express genes encoding enzymes involved in carcinogenesis, such as prostaglandin-endoperoxide synthase (PGHS2; COX2), NADPH oxidases, and spermine oxidase. The products of these enzymes (prostaglandins, O2D, and H2O2 plus 3-aminopropanal) lead to formation of dicarbonyl electrophiles: levuglandins (LGs), malondialdehyde (MDA), 4-oxo-nonenal (4-O NE), and acrolein. Electrophiles may lead to immune dysfunction and neoplastic risk by forming adducts with proteins and DNA11-15. However, the role of these reactive aldehydes in colon carcinogenesis is previously unknown. The present inventors have discovered that the level of LG-protein adducts is increased in the colon tissues of i) human ulcerative colitis (UC), colitis-associated carcinogenesis (CAC), and CRC; ii) mice treated with azoxymethane-dextran sulfate sodium (AOM-DSS), a model of CAC; and iii) transgenic mice with a tamoxifen-inducible disruption of Apc using the colon-specific, caudal type homeobox 2 (CDX2) Cre (CDX2P-CreERT2;Apcff), which recapitulates sporadic/genetically-driven CRC. The present inventors have also discovered that compounds of the present invention, including 2-hydroxybenzylamine (2-HOBA) (salicylamine) and 5-ethyl-2-hydroxybenzylamine (EtHOBA) react with dicarbonyl electrophiles at a rate 3 orders of magnitude faster than lysine, thus preventing adduct formation with cellular macromolecules. 2-HOBA is a natural product derived from buckwheat seeds. It is not toxic or mutagenic and protects mice from oxidative damage in models of hypertension and Alzheimer's disease. A phase I clinical safety trial in humans has been completed at Vanderbilt University Medical Center (VUMC; NCT03176940)19, and other trials are ongoing. Additionally, the present inventors show that compounds of the present invention significantly reduce tumor development and dysplasia in the AOM-DSS model. The present inventors also show that mice treated with compounds of the present invention show increased colonic immune responses to tumors.

Cyclooxygenase-2 (COX-2) expression is associated with the development of many cancers, and the enzyme plays a key role in the progression of chronic gastrointestinal inflammation to cancer. Predictably, treatment with COX inhibitors decreases a person's total risk of cancer. Prevention studies as well as animal models suggest that increased COX-2 activity is both an early event in carcinogenesis, which contributes to the cellular transformation to malignancy, as well as a sustained event in some colorectal and lung cancers that can be associated with metastasis and poorer clinical prognosis. As predicted by these data, inhibiting COX-2 activity with non-steroidal anti-inflammatory drugs (NSAIDS) or COX-2-specific inhibitors over time reduces a person's total risk of colon, breast, lung, and prostate cancers.

Despite the promise of these drugs in cancer prevention, the gastrointestinal toxicity associated with long-term NSAID treatment and increased cardiovascular events associated with COX-2-specific inhibitors limit their clinical use. A better understanding of the specific downstream contributions of COX-2 to carcinogenesis could lead to new treatments that bypass these undesirable effects.

The product of COX-2, prostaglandin $H_2(PGH_2)$, is converted enzymatically into other prostaglandins, and indeed $PGE_2$ is a well-described promoter of carcinogenesis. However, depending on the animal model, deletion of microsomal $PGE_2$ synthase-1 can either prevent or accelerate tumorigenesis, indicating that the contribution of COX-2 to cancer, particularly to cellular transformation, is probably multifaceted.

Figure 1:
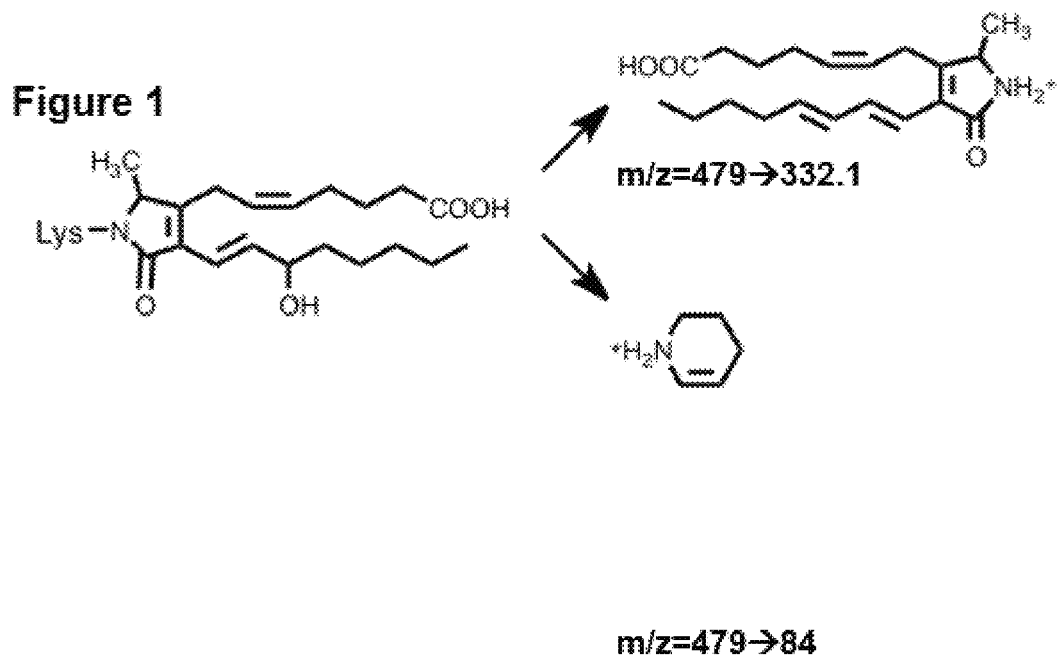
FIG. 1 shows a scheme and structure of the LG-lysyl adduct and the fragment ions monitored in positive ion mode (+H).

Besides enzymatic conversion, $PGH_2$ also spontaneously rearranges in aqueous solution to form the highly reactive levuglandins, $LGE_2$ and $LGD_2$. The levuglandins (LGs) constitute about 20% of total $PGH_2$ rearrangement products. Newly formed LGs react almost immediately with free amino groups, such as those in lysine, which leads to stable covalent LG-protein adducts measureable by mass spectrometry (FIG. 1) or protein-protein crosslinks. Following COX-2 activity, LG adducts of protein form in cells and in tissues. Proteins rich in lysine are thus especially susceptible to adduction, and due to the perinuclear localization of COX-2 and a $PGH_2$ half-life measured in minutes, we speculated that it would be possible for $PGH_2$ to cross the nuclear envelope before rearranging to $LGE_2$, allowing formation of LG adduct on the lysine-rich histones.

The present inventors have discovered LG-histone adducts in multiple cancer cell lines as well as rat liver, with highest measurable amounts of adduct on the H4 histone. Adduct formation is dependent on COX-2 expression or activity. Lysines, with their short sidechain and positive charge, are critical for histone ionic interaction with DNA, and the inventors find that this interaction is decreased with the introduction of a hydrophobic negative charge from LG. Covalent histone modifications are a major method of controlling gene expression. Changes to lysyl modifications of histones are associated with human cancer. These findings link COX-2 induction with perturbation of normal DNA-histone interactions and provide a novel role for the enzyme in carcinogenesis.

Importantly, the inventors have found a small-molecule salicylamine derivative that scavenges LG to reduce adduct formation on histones without affecting COX-2 activity. In comparison with other scavengers, salicylamine, pyridoxamine and their other analogues, ethylsalicylamine was most potent in protecting histones from modification by levuglandins, indicating that it has the key property of being transported into the nucleus.

As stated above, *Helicobacter pylori* (Hp) induces an innate immune response in epithelial and myeloid cells that leads to inflammation-associated cancer. The inflammatory effector molecules, such as prostaglandins and reactive oxygen species, can generate the bifunctional electrophiles: levuglandins (LG), malondialdehyde, 4-oxo-nonenal, and acrolein. These molecules form covalent adducts on DNA bases and on lysines (Lys-LG) in histones, thus disrupting DNA/histone interactions and increasing risk for mutations. Embodiments of the present invention scavenge said electrophiles, including 5-ethylsalicylamine (EtSA), for example, which prevents adduct formation.

As discussed further in the Examples, the human gastric epithelial cell line AGS was infected with Hp PMSS1±10 mM EtSA. FVB/N insulin-gastrin (INS-GAS) mice and Mongolian gerbils were infected for 8 wk with Hp PMSS1 and 7.13, respectively; EtSA (0.75% in water) was given to animals beginning one wk post-infection. Lys-LG adducts, a marker of electrophile reactions, and EtSA were quantified by LC/EST/MS/MS. Histology was analyzed on H&E staining. DNA damage was evaluated by pH2AX staining. Hp colonization was quantified by culture. Mucosal immune responses were determined by RNA profiling and by Luminex assay. Mice were imaged using PET/CT with $^{18}$F-FDG (inflammation marker) and $^{18}$F—NaF (tumor marker).

Lys-LG adduct levels were increased in AGS cells infected with Hp and inhibited by EtSA. Similarly, Lys-LG adducts were significantly increased by 2.3-fold in infected mice compared to uninfected animals (p<0.05), and were completely inhibited by EtSA, which was found to be bioavailable in the stomach. There were decreases in frequency of intramucosal carcinoma (from 69% to 28%;

p<0.05) and extent of dysplasia and carcinoma (p<0.05) in Hp-infected INS-GAS mice treated with EtSA. DNA damage was increased by 5.8-fold in infected mice and was decreased by 71% with EtSA treatment (p<0.05). Levels of Hp colonization, histologic gastritis, and tissue cytokines and chemokines were not affected by EtSA in INS-GAS mice. These data were confirmed by imaging: gastric uptake of the tumor marker $^{18}$F—NaF was induced by Hp and decreased by EtSA, while uptake of the inflammation marker $^{18}$F-FDG was increased in infected mice, but not modified by EtSA. Similarly, the frequency of gastric cancer development was reduced in gerbils treated with EtSA.

This shows that Hp-induced gastric carcinogenesis is inhibited by the electrophile scavenger EtSA, without affecting inflammation. Thus, without being bound by theory or mechanism, embodiments of the present invention act downstream of inflammatory reactions by removing electrophiles, which are a link between inflammation and the molecular alterations that lead to neoplastic transformation. The electrophile scavengers of the present invention serve as valuable chemopreventive agents.

Compounds

It is understood that the following disclosed compounds can be employed in the disclosed methods of using or treating.

Examples of these compounds include, but are not limited to, compounds selected from the formula:

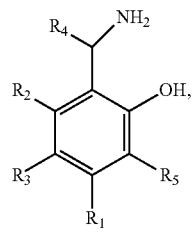

wherein:

$R_1$ is H, D, $D_2$, substituted or unsubstituted alkyl, substituted or unsubstituted alkoxy, carboxyl, substituted or unsubstituted aryl, or substituted or unsubstituted cycloalkyl;

$R_2$ is H, substituted or unsubstituted alkyl, substituted or unsubstituted alkoxy, alkyl-alkoxy-$R_4$;

$R_3$ is H, halogen, substituted or unsubstituted alkyl, substituted or unsubstituted alkoxy, hydroxyl, nitro;

$R_4$ H, D, $D_2$, substituted or unsubstituted alkyl, substituted or unsubstituted alkoxy, carboxyl, substituted or unsubstituted aryl, or substituted or unsubstituted cycloalkyl;

$R_5$ is H, substituted or unsubstituted alkyl, substituted or unsubstituted alkoxy; or analogs thereof; and pharmaceutical salts thereof.

Without being bound by theory or mechanism, certain $R_4$ substituents are believed to impede metabolism by monoamine oxidase.

Examples of these compounds also include, compounds selected from the formula:

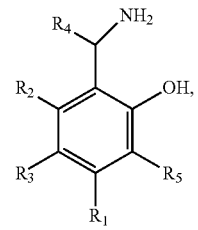

wherein:

$R_1$ is $CH_3$ or alkyl;

$R_2$ is H, substituted or unsubstituted alkyl, substituted or unsubstituted alkoxy, alkyl-alkoxy-$R_4$;

$R_3$ is H, halogen, substituted or unsubstituted alkyl, substituted or unsubstituted alkoxy, hydroxyl, nitro;

$R_4$ is a $CH_3$ or alkyl;

$R_5$ is H, substituted or unsubstituted alkyl, substituted or unsubstituted alkoxy;

or analogs thereof; and pharmaceutical salts thereof.

In other embodiments, $R_2$ is H, $R_5$ is H, and $R_4$ is $CH_3$.

Further examples of compounds or analogs of the present invention include compounds of the following formula:

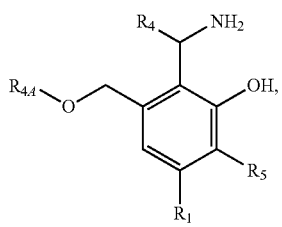

wherein $R_1$, $R_4$, and $R_6$ are defined above. $R_{4A}$ is independent from $R_4$ and is H, D, substituted or unsubstituted alkyl, substituted or unsubstituted alkoxy, carboxyl, substituted or unsubstituted aryl, or substituted or unsubstituted cycloalkyl; or an analog thereof, and pharmaceutical salts thereof.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, optionally substituted alkyl, cycloalkyl, alkoxy, amino, ether, halide, hydroxy, nitro, silyl, sulfo-oxo, or thiol as described herein.

The term "alkoxy" group includes an alkyl group as defined above joined to an oxygen atom having preferably from 1 to 10 carbon atoms in a straight or branched chain, such as, for example, methoxy, ethoxy, propoxy, isopropoxy (1-methylethoxy), butoxy, tert-butoxy (1,1-dimethylethoxy), and the like.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The terms "amine" or "amino" as used herein are represented by a formula $NA^1A^2A^3$, where $A^1$, $A^2$, and $A^3$ can be, independently, hydrogen or optionally substituted alkyl, cycloalkyl, alkenyl, cycloalkenyl, alkynyl, cycloalkynyl, aryl, or heteroaryl group as described herein.

Examples of compounds or analogs of the present invention include compounds of the following formula:

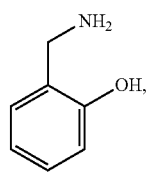

or an analog thereof, and pharmaceutical salts thereof.

Further examples of compounds or analogs of the present invention are 2-hydroxybenzylamine, methyl-2-hydroxybenzylamine, and ethyl-2-hydroxybenzylamine.

Further examples of compounds or analogs of the present invention include compounds of the following formula:

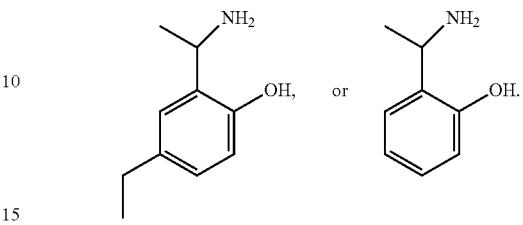

or an analog thereof, and pharmaceutical salts thereof.

Further examples of compounds or analogs of the present invention include compounds of the following formula:

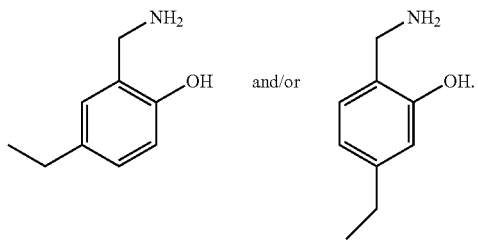

Further compounds or analogs may also be chosen from:

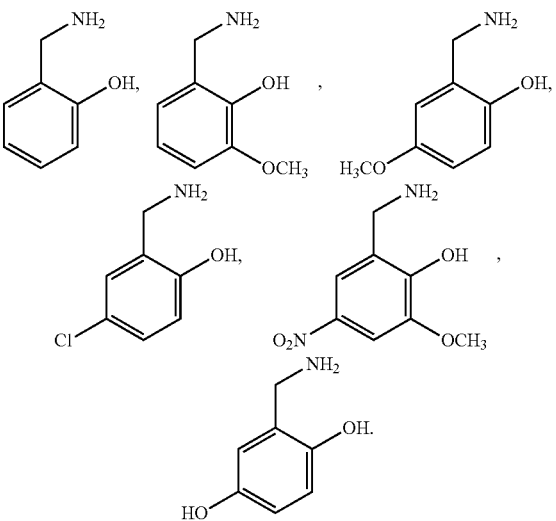

or an analog thereof.

The compounds may also be chosen from:

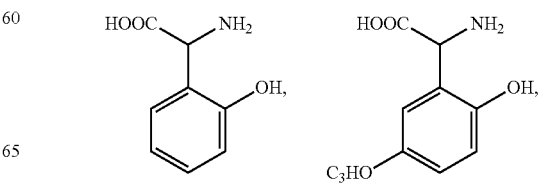

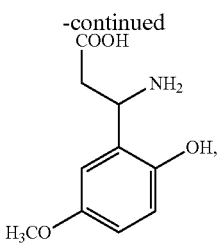

or an analog thereof.

The compounds of the present invention can also be chosen from:

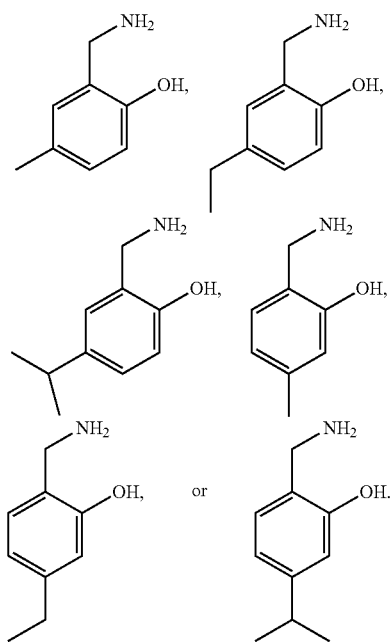

The compounds of the present invention can be administered as the sole active pharmaceutical agent, or can be used in combination with one or more other agents useful for treating or preventing various complications, such as, for example, lesions and cancer. When administered as a combination, the therapeutic agents can be formulated as separate compositions that are given at the same time or different times, or the therapeutic agents can be given as a single composition.

The compounds of the present invention may be made up in a solid form (including granules, powders or suppositories) or in a liquid form (e.g., solutions, suspensions, or emulsions). They may be applied in a variety of solutions and may be subjected to conventional pharmaceutical operations such as sterilization and/or may contain conventional adjuvants, such as preservatives, stabilizers, wetting agents, emulsifiers, buffers etc.

For administration, the compounds of the present invention are ordinarily combined with one or more adjuvants appropriate for the indicated route of administration. For example, they may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol, and tableted or encapsulated for conventional administration. Alternatively, they may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

In therapeutic applications, the compounds of the present invention may be administered to a patient in an amount sufficient to reduce or inhibit the desired indication. Amounts effective for this use depend on factors including, but not limited to, the route of administration, the stage and severity of the indication, the general state of health of the mammal, and the judgment of the prescribing physician. The compounds of the present invention are safe and effective over a wide dosage range. However, it will be understood that the amounts of compound actually administered will be determined by a physician, in the light of the above relevant circumstances.

The compounds of the present invention may be administered by any suitable route, including orally, parentally, by inhalation or rectally in dosage unit formulations containing conventional pharmaceutically acceptable carriers, adjuvants, and vehicles, including liposomes. The term parenteral as used herein includes, subcutaneous, intravenous, intraarterial, intramuscular, intrastemal, intratendinous, intraspinal, intracranial, intrathoracic, infusion techniques, intracavity, or intraperitoneally. In a preferred embodiment, ethylsalicylamine is administered orally or parentally.

Pharmaceutically acceptable acid addition salts of the compounds suitable for use in methods of the invention include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate, n-methyl glutamine, etc. (see, e.g., Berge et al., J. Pharmaceutical Science, 66: 1-19 (1977).

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

EXAMPLES

The following examples and discussion are to be construed as being exemplary of the present invention, and not intended to be limiting thereof.

Example 1. Increased Electrophile Adduct Formation in Patients with CAC

Figure 2:
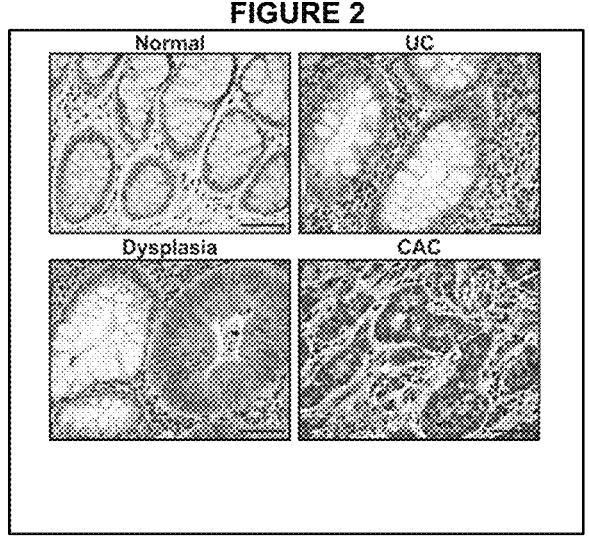
FIG. 2 shows immunohistochemistry for LG-protein adducts, human colon TMA. Scale bar, 50 µm.

The present inventors performed immunohistochemistry (IHC) staining using the single chain antibody (Ab) D11, which specifically binds to L G-protein adducts, and a tissue microarray (TMA) from VUMC that contains colon tissues from patients with ulcerative colitis (UC), and associated precancerous and cancerous lesions. Histopathologic diagnoses were established from clinical case material from surgical resections and confirmed by H&E staining of the TMA. High levels of L G-protein adducts were present in active colitis, dysplasia, and carcinoma compared to normal patients (FIG. 2). On the TMA, 7/9 (78%) high grade dysplasia (HGD) cores and 21/23 (91%) CAC cores were scored positive for L G adducts. The strongest nuclear staining was observed in patients with CAC (FIG. 2), supporting the concept that electrophiles may thus affect histones and DNA.

Example 2. Bioavailability of EtHOBA in the Colon

Figures 3A, 3B:
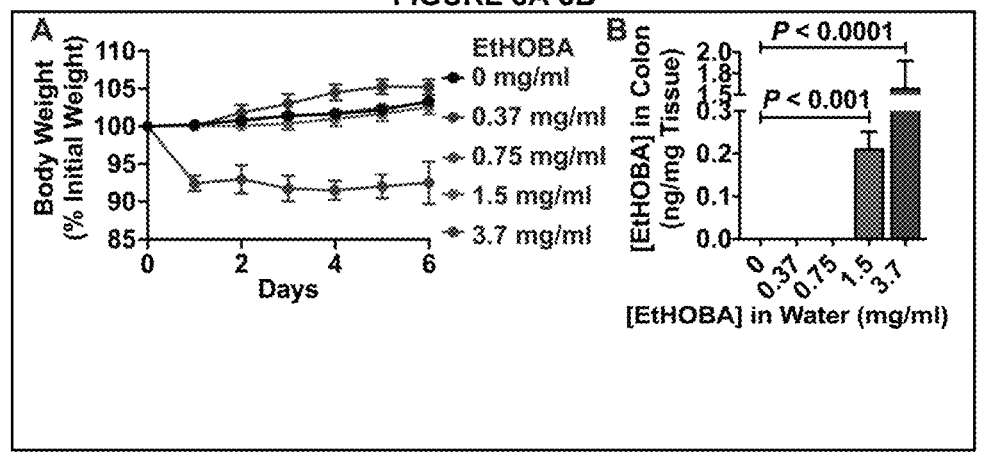
FIGS. 3A and 3B show data from C57BL/6 mice were treated or not with various concentrations of EtHOBA. (A) Body weight was assessed every day. (B) After 6 days, mice were euthanized and EtHOBA was measured in the colon. n=5 mice/group.

The present inventors analyzed the effect of various concentrations of EtHOBA and its bioavailability in control mice. Animals that were given 3.7 mg/ml EtHOBA lost weight on day 1, but did not lose additional weight and did not die (FIG. 3A). Mice treated with 0.37-1.5 mg/ml had no loss of body weight compared to untreated mice (FIG. 3A). After 6 days of treatment, EtHOBA concentrations in the colon were analyzed using liquid chromatography electrospray ionization tandem mass spectrometry (LC/EST/MS/MS). The EtHOBA scavenger was readily detected in mice treated with 1.5 and 3.7 mg/ml (FIG. 3B). There was i) no macroscopic evidence of organ damage and ii) no change in colon weight/length in mice treated with 1.5 or 3.7 mg/ml EtHOBA (not shown).

Example 3. Compounds of the Present Invention Reduce the Development of CAC

Figure 4:
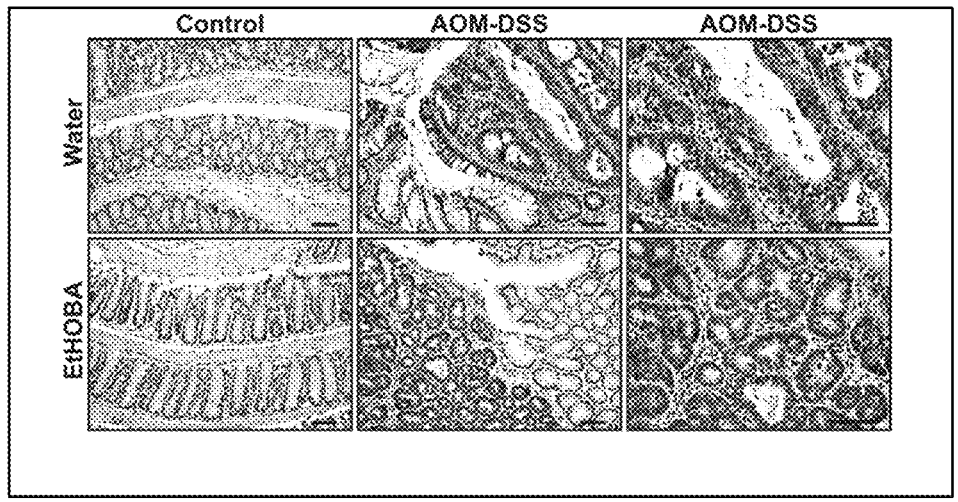
FIG. 4 shows immunohistochemistry for LG-protein adducts. Scale bar, 50 µm.
Figures 5A, 5B, 5C, 5D, 5E, 5F, 5G:
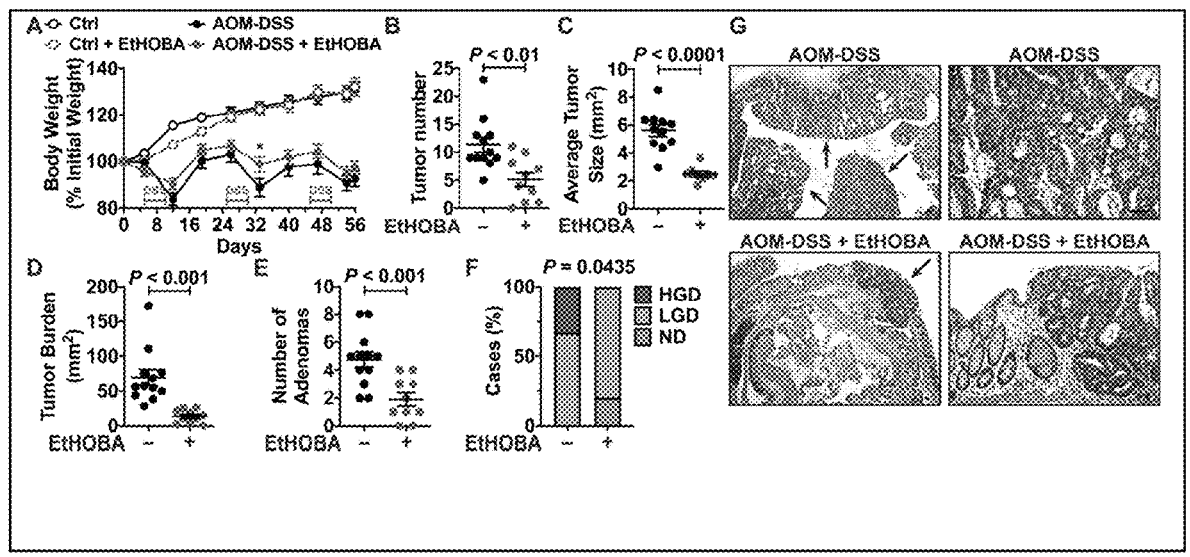
FIGS. 5A, 5B, 5C, 5D, 5E, 5F, and 5G show mice (n=10-12/group)±AOM-DSS±1.5 mg/ml EtHOBA. (A) Body weight; "P<0.05 compared to AOM-DSS-treated mice. (B) Tumor number. (C) Average tumor size per mouse. (D) Tumor burden. (E) Number of adenomas. (F) Frequency of diagnoses; ND, no dysplasia. (G) H&E staining; each arrow depicts a tumor. Scale bar, 50 µm.

Animals receive an i.p. injection of the carcinogen AOM (12.5 mg/kg) followed by 3 cycles of 4% DSS, each for 4 days, over a total of 56-77 days. To directly determine the role of electrophiles in colon carcinogenesis, the present inventors tested the effect of EtHOBA in C57BL/6 mice in the AOM-DSS model. Mice were given 1.5 mg/ml EtHOBA one day after AOM and continued throughout the experiments, except during the DSS cycles, to avoid mixing. The present inventors assessed electrophiles in colons of mice treated with AOM-DSS, by IHC for electrophile protein adducts. There was markedly increased staining in mice with experimental CAC compared to control animals, predominantly in tumor areas (FIG. 4), including strong epithelial nuclear staining, indicating that electrophiles reach the nucleus and can affect histones and DNA. There was a marked attenuation of L G-protein adducts in mice treated with the EtHOBA electrophile scavenger (FIG. 4). There was no change in body weight in control mice treated for 56 days with EtHOBA (FIG. 5A), as with the acute treatment (FIG. 3A). At each cycle of DSS, mice had a decrease of body weight (FIG. 5A); there was less weight loss in animals given EtHOBA (FIG. 5A). Most importantly, there were significantly less tumors (FIGS. 5B, 5F), lower tumor size (FIG. 5C) and total tumor burden (FIG. 5D), and a reduced number of histologic adenomas (FIG. 5E) in the AOM-DSS group treated with EtHOBA. Histologic assessment further revealed that all the mice treated with AOM-DSS alone had either high grade dysplasia (HGD), or low-grade dysplasia (L GD; FIGS. 5F-G). In total, without the scavenger treatment, 25% of mice had HGD and the remaining 75% had L GD; in contrast, in those receiving EtHOBA, 20% had no dysplasia, none had HGD, and 80% had only L GD, a significant overall difference in diagnoses (FIGS. 5F-G). These data indicate that scavenging of electrophiles by EtHOBA can lead to reduction of inflammation-induced neoplastic transformation in the colon.

Figure 6:
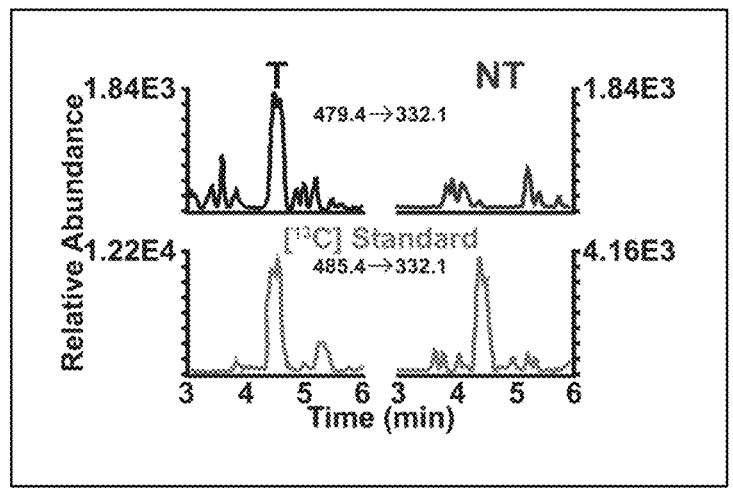
FIG. 6 shows representative data of levels of lysyl-L G adducts in the colon of CRC patients. Adducts isolated from tumor (T) or non-tumor (NT) biopsies were analyzed by LC/EST/MS/MS.

Example 4. Increased Electrophile Adduct Formation in Patients with Colon Cancer The present inventors analyzed the abundance of lysyl-L G adducts by LC/ESI/MS/MS11,12 in tumor and non-tumor tissues (from our collaborator, Dr. K. Washington) from patients with sporadic CRC. The level of lysyl-L G adducts in tumors was higher than in normal tissues (FIG. 6), supporting the concept that electrophiles and their adducts are generated in the human colonic mucosa and are reactive in tumors. This also demonstrates that lysyl-L G adducts can be measured from colon tissues using LC-MS, which is needed for this project.

Figures 7A, 7B, 7C:
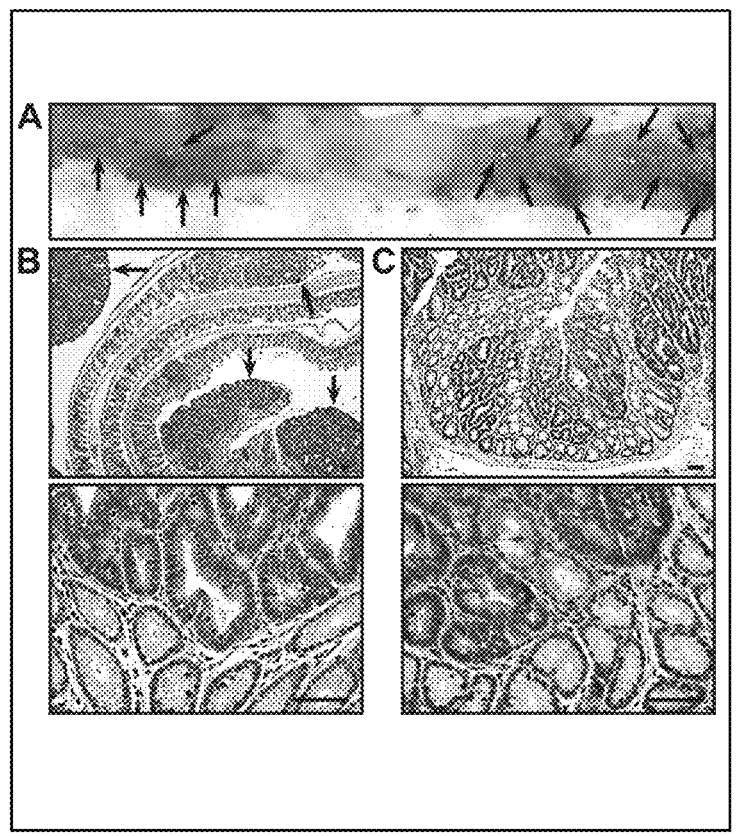
FIGS. 7A, 7B, and 7C show data related to CDX2P-CreER$^{T2}$;Apc$^{fl/fl}$ mice (n=5) treated with 25 mg/kg tamoxifen. At day 33, animals were euthanized. (A) Colon, from proximal (left) to rectum (right), showing tumors (arrows).

Example 5. Lysyl-LG Adducts are Increased in Mice with a Model of Enetic/Sporadic Colon Cancer To mimic human CRC associated with APC loss, the present inventors used C57BL/6 CDX2P-CreER$^{T2}$; Apc$^{fl/fl}$ mice. APC loss is a sentinel event in CRC, due to germline transmission as in FAP or its variants (e.g. attenuated FAP) with 100% penetrance. It is also a hallmark of sporadic CRC. This mouse model has been developed and optimized over the last decade. A major advance has been the use of the Apc double-floxed mice (Apc$^{fl/fl}$) mouse, which greatly increases the speed of tumor penetrance compared to the single flox (Apc$^{fl/+}$), combined with the tamoxifen inducible Cre, which allows for precise control and timing of the model. A single dose of 25 mg/kg i.p. of tamoxifen for these mice. These mice lose Apc gene function in the colon when treated with tamoxifen and exhibit tumors. The present inventors have found that mice show a 100% penetrance of tumors in male mice after tamoxifen, with many colon and rectal tumors seen (FIG. 7A). Histologically, the adenomatous tumors are large and readily detected on Swiss-rolls, with features of high-grade dysplasia (FIG. 7B). To verify the generation of electrophiles in this genetic/sporadic CRC model, the present inventors stained the colon of the tamoxifen-induced CDX2P-CreER$^{T2}$;Apc$^{fl/fl}$ mice using the D11 antibody. Dysplastic glands displayed marked staining for L G protein adducts compared to surrounding areas (FIG. 7C) and to control animals (not shown).

Example 6. An Electrophile Scavenger Increases Immune Cell Infiltration in Mice with CAC The present inventors used the tissues generated for FIG. 5 to study immune cell responses in AOM-DSS-treated mice±EtHOBA. It was discovered that more influx of immune cells in mice treated with EtHOBA compared to untreated mice (FIG. 8). EtHOBA had no effect on histology in control mice (not shown). Together with the data depicted in FIG. 5, results indicate that the electrophile scavenger both reduces the development of tumors in the AOM-DSS model and stimulates immune cell response. Because scavenging of electrophiles led to more immune cells in the colon, this suggests that electrophiles dampen mucosal immune responses.

Example 7. The Colonic Antitumoral Immune Response is Increased by EtHOBA

Using the tissues from the same mice as in FIG. 5, the present inventors analyzed the expression of key genes encoding mediators of the innate and adaptive immune response. The transcripts of the prototype i) M1 macrophage cytokines IL-1β (Il1b), TNF-α (Tnfa), IL-12A (Il12a), and IL-12B (Il12b), and the enzyme NOS2 (Nos2); ii) M2 macrophage enzyme ARG1 (Arg1), iii) Th1 cytokine IFN-γ (Ifng), and iv) Th17 cytokine IL-17 (Il17) were each significantly induced in the non-tumor and tumor tissues of AOM-DSS-treated mice compared to control animals (FIG. 11). Importantly, the overall pattern was that the genes encoding antitumoral effectors were expressed at a higher level in mice that were given compounds of the present invention. The following reached statistical significance for an increase with EtHOBA treatment: Tnfa (tumor), Nos2 (tumor), Il12a (non-tumor and tumor), Il12b (tumor), and Il17 (non-tumor) in this experiment (FIG. 9), which was limited by the reduced number of mice in the EtHOBA group with tumors. In contrast, the gene encoding the immunosuppressive myeloid mediator AR G1 was not affected by EtHOBA (FIG. 9). Using IF, we confirmed that mice treated with AOM-DSS mice that were given EtHOBA had increased $CD68^+NOS2^+$ (M1 macrophages) in colon tumors (FIG. 10).

These results suggest that the treatment of mice with experimental CAC with an electrophile scavenger exhibit more innate immune responses, including in the tumors, and potentially enhanced adaptive immune responses. Because compounds of the present invention reduce the number and progression of tumors in the colon (FIG. 5), one mechanism of action may be restoration of antitumoral immunity. The present inventors previously reported that mice with myeloid-specific deletion of ornithine decarboxylase, the rate-limiting enzyme for polyamine synthesis, developed less tumors in the AOM-DSS model—a finding that was strongly associated with enhanced immune cell infiltration in the non-tumor area and increased M1 cytokines and NOS233. These results indicated that polyamines impair antitumoral

Example 8. COX-2 Activity and Histone Adduction

Experimental Procedures
Materials

All reagents and chemicals were purchased from Sigma-Aldrich (St Louis, Mo.) unless otherwise noted. Methanol and acetonitrile were from Fisher Scientific (Pittsburgh, Pa.) and were HPLC grade or higher. [14C]-arachidonic acid (AA) was obtained from Perkin-Elmer Life Sciences (Boston, Mass.). The following reactive dicarbonyl scavenger molecules were synthesized by V. Amarnath as previously described: pentylpyridoxamine (PPM), 3-methoxysalicylamine (3-MoSA), and 5-ethyl salicyl amine (EtSA).

Treatment of Cells

To stimulate COX-2 expression, A549 or RAW264.7 cells were treated overnight with 5 ng/mL IL-1B (A549) or 10 μg/mL LPS and 10 U/mL IFNγ (RAW264.7) in serum-free medium. When indicated, cells were pretreated with indomethacin, aldehyde scavengers (glucosamine, 3-MoSA, PPM or EtSA), or vehicle (ethanol for indomethacin, $H_2O$ for scavengers) for 45 min, and then given 20 μM arachidonic acid (AA) or DMSO vehicle for 1 h before lysing.

Histone Extraction

Cultured cells were lysed in hypotonic buffer (10 mM Tris/10 mM NaCl/3 mM $MgCl_2$) containing 1 mM pyridoxamine and 100 μM indomethacin to prevent the artifactual formation of $LGE_2$ during the lytic process. After letting cells swell on ice, membranes were disrupted by addition of Triton X-100 (0.5% final concentration) and vortexing. Nuclei were isolated by centrifugation for 10 min at 1000×g, and the resulting pellet washed with PBS. Histones were extracted in 0.4 N $H_2SO_4$, precipitated with trichloracetic acid, and washed with acetone. With this method, histones are the predominant proteins and contaminating nuclear proteins are reduced (FIG. 3A). Histones were resolubilized in dilute NaOH, and pH neutralized with HCl. Protein concentration was determined using the method of Bradford. For tissue, a portion of frozen liver was homogenized in buffer containing 40 mM sodium citrate, and 1% Triton X-100 with 3 mM Trolox and 100 μM indomethacin. The supernatant was separated from settled debris, and nuclei were pelleted at 500×g and washed. Nuclear pellets were frequently transferred to fresh tubes to avoid contamination by floating lipid debris; any remaining was removed with a cotton swab. Histones were extracted as above. All centrifugation steps were carried out at 4° C.

Sample Preparation and Mass Spectrometry

Histone samples were prepared for mass spectrometry by addition of ammonium bicarbonate to 5 mM final concentration before digesting to single amino acids by protease step-digestion as previously described. In the case of immunoblots, proteins were digested directly off the nitrocellulose through incubation of the nitrocellulose strip in 30 μg/mL Pronase in ammonium bicarbonate buffer, and later addition of aminopeptidase. All samples were centrifuged at 2000×g for 10 min. after final digestion to remove precipitate, spiked with 0.2 ng $^{13}$C-lysyl-lactam internal standard, and purified on prepared tC18 cartridges (Waters Corp., Milford, Mass.). Samples on tC18 cartridges were washed with water, then 30% methanol, before being eluted in 80% methanol and concentrated by evaporation. Samples were evaluated by electrospray ionization (ESI) LC/MS/MS on a ThermoFisher TSQ Quantum triple quadrapole mass spectrometer in positive ion mode and quantitated by isotopic dilution as previously described, with the exception of a reduced flow rate of 0.1 mL/min.

Measurement of $PGE_2$

A sample of cellular media was taken just prior to lysis and centrifuged to remove any cellular debris. For $PGE_2$ analysis, samples were spiked with 2 ng of $[^2H_7]$ $PGE_2$ as an internal standard. Prostaglandins were isolated and derivatized for analysis by GC/MS, operating in negative ion chemical ionization (NICI) mode and monitoring selected ions as previously described. For the $[^2H_4]$ $PGE_2$ internal standard, m/z=528. To account for the deuterium-protium exchange at the position C12 of $[^2H_7]$ $PGE_2$, the summation of the signals obtained at m/z=530, m/z=531 and m/z=532 was performed.

Autoradiography

A549 or RAW264.7 cells were treated overnight to stimulate COX-2 expression and given 20 μM $^{14}$C-AA (116 μCi)

for 1 h. Histones were isolated as described above and separated on 4-12% SDS-PAGE gels (Life Technologies), which were stained with Coomassie and exposed to film for 2 weeks.

Salt Extraction 60-80% confluent A549 cells were stimulated and treated with AA±500 µM EtSA before scraping cells in lysis media for nuclear isolation as above. After addition of Triton X-100 and vortexing, 1.5 mL of each sample was aliquoted into an eppendorf and centrifuged to separate nuclei. Pellets were washed with PBS and all buffer removed. Nuclear pellets were resuspended in extraction buffer containing 0.6M, 0.9M, 1.2M or 1.5M NaCl (with 10 mM Tris, pH 7.5, 3 mM $MgCl_2$, 0.5% NP-40, and protease inhibitor cocktail) and incubated 10 min on ice. Following this extraction period, the nuclei were centrifuged at 16,000×g to obtain the soluble fraction. This was sonicated, denatured at 95° C., and analyzed by SDS-PAGE and Western blotting, using Ponceau stain to visualize proteins and confirm equal loading, and anti-H4 antibody (Abcam, Cambridge, Mass.).

Statistical Analyses

All data were analyzed using Prism software (GraphPad, La Jolla, Calif.). Data are expressed as means±SE, and statistical significance was determined using one-way ANOVA followed by Tukey's post-test or Dunnett's multiple comparisons post-test, when appropriate. A p value<0.05 was considered significant.

Results

Levuglandins Form Adducts on Histones in Cultured Cell and Whole Tissue

Figures 11A, 11B, 11C, 11D, 11E, 11F:
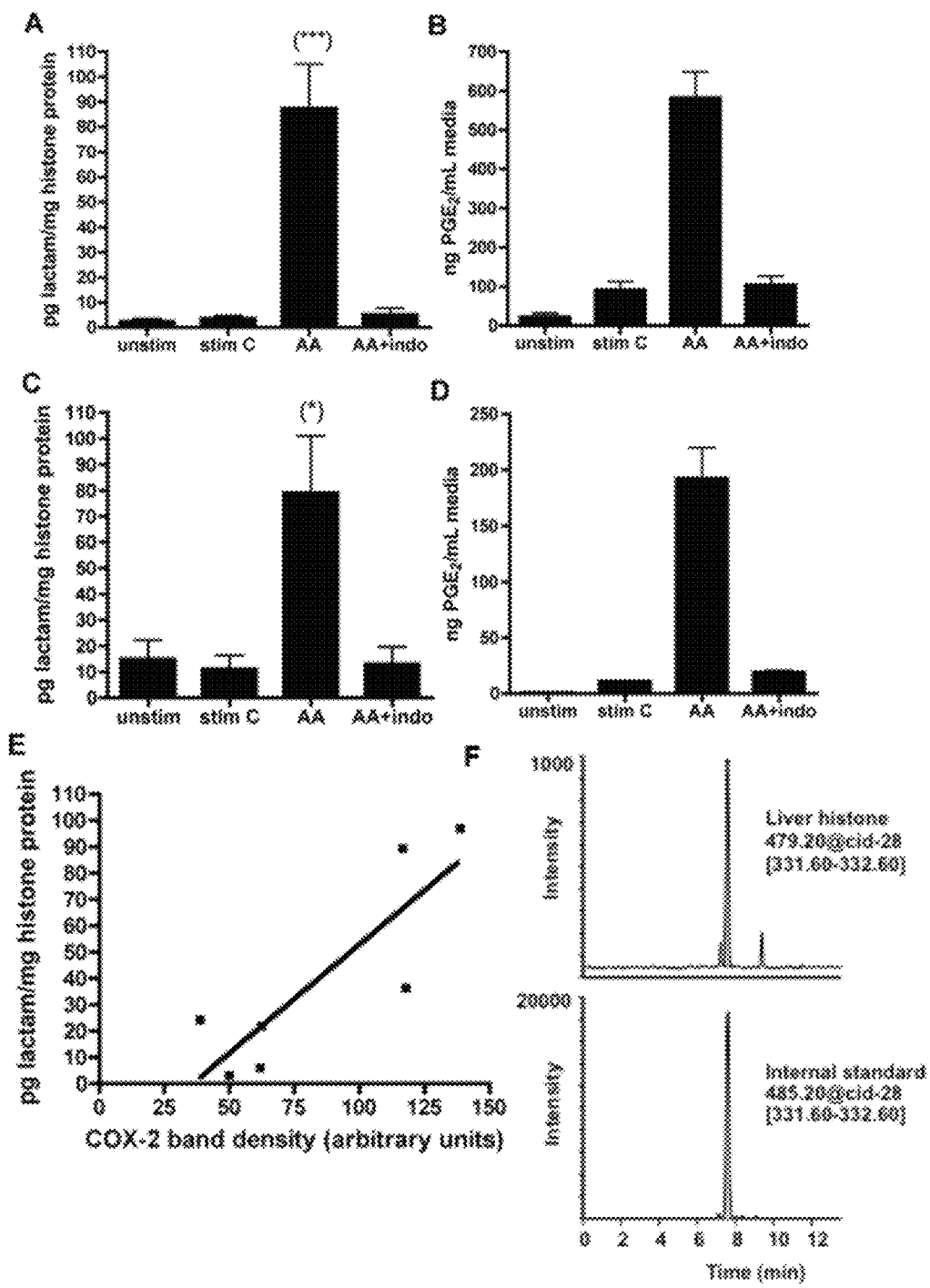

With mass spectrometry, the present inventors identified LG-lysyl adducts on histones in RAW264.7 macrophages (FIG. 11A) as well as A549 cultured lung epithelial cells (FIG. 11C). COX-2 is upregulated in these cells upon cytokine stimulation, and addition of exogenous AA leads to formation of LG-histone adducts. Formation of these adducts is blocked with indomethacin, further indicating a COX-dependent mechanism (FIGS. 11A and 11C). Very few LG-histone adducts are formed in these cell lines without addition of exogenous AA, and $PGE_2$ analysis of cell media from each group indicates there is comparatively little endogenous AA mobilized following induction of COX-2 (FIGS. 11B and 11D). Although few adducts are formed at basal levels in our cell lines, we find the LG-lysyl adduct in rat liver histones (FIG. 11E), where levels correlate with COX-2 expression, demonstrating COX-2-dependent adduct formation under physiological conditions.

LG-Histone Adducts are Restricted to Specific Histone Isoforms

Figures 12A, 12B, 12C, 12D:
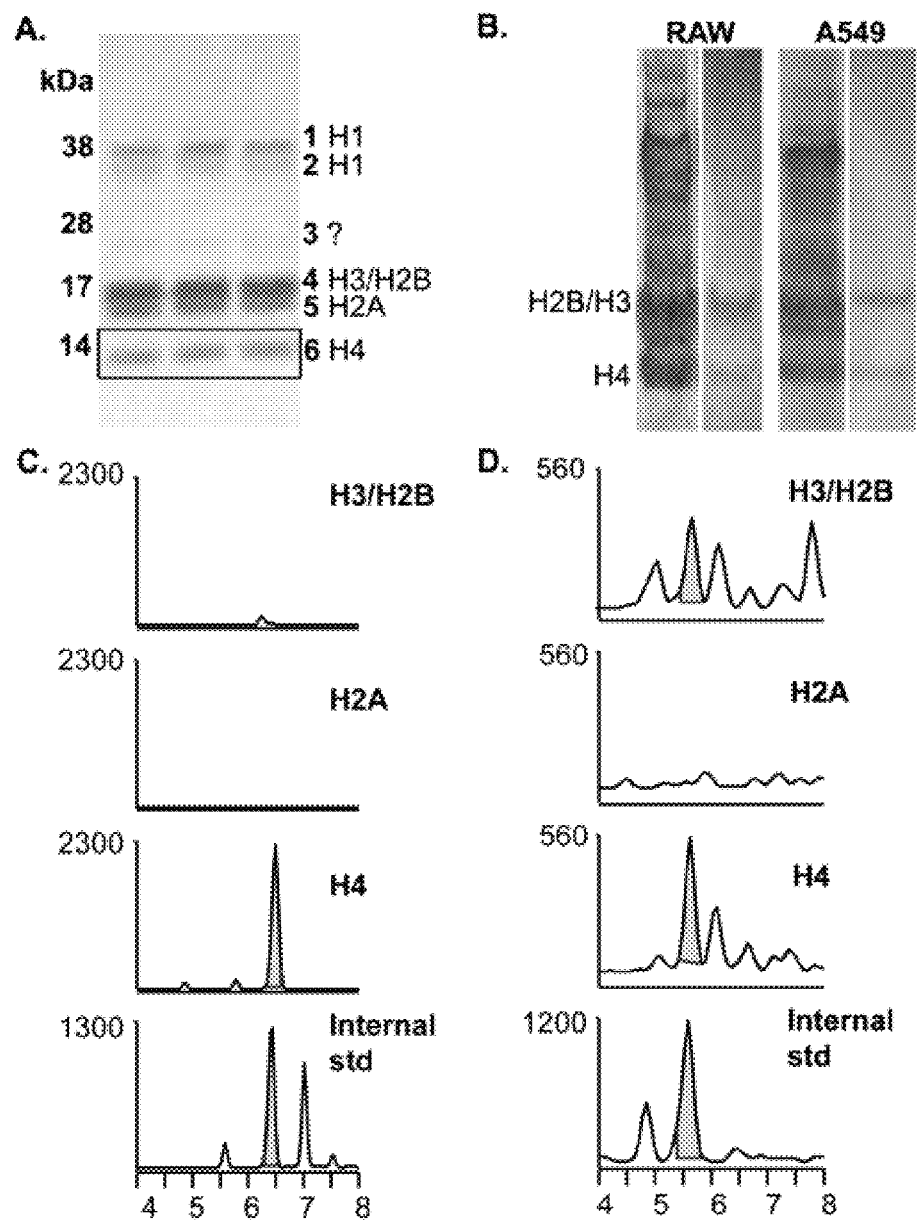

Using 0.4N $H_2SO_4$ to extract histones results in a relatively pure preparation, with histones corresponding to known molecular weights (FIG. 12A). Incubation of $^{14}C$-AA with stimulated A549 or RAW264.7 cells led to a $^{14}C$-containing band in the histone preparation that corresponded with H4 and H3/H2B, despite the fact that other histones are represented in equal or greater quantity (FIG. 12B). The present inventors treated stimulated RAW264.7 macrophages or A549 lung carcinoma cells with 20 µM AA for 1 h and directly digested and analyzed the SDS-PAGE bands as labeled in FIG. 12A. The H4 band yielded a predominant peak corresponding with the internal LG-lysyl standard, while lower or no signal was seen in the H3/H2B band and no corresponding peaks were seen in other bands (FIGS. 12C and 12D, data not shown). Thus, there is consistent evidence for formation of an LG-lysine lactam adduct on H4. The radiolabeled AA product adducted to H3/H2B probably includes structures in addition to the LG-lysine lactam. These results, from two separate cell lines, suggest that there is specificity in the reaction of LG with histones.

The Scavenger 5-Ethylsalicylamine (EtSA) Reduces LG-Histone Adduct Formation without Affecting COX-2 Activity As demonstrated herein, in RAW264.7 cells, 5-ethylsalicylamine (EtSA) most effectively blocked adduct formation. Pentylpyridoxamine partially inhibited histone adduct formation, but was much less potent than 5-ethylsalicylamine (FIG. 13A). EtSA also inhibited LG-histone adduct formation in stimulated, AA-treated A549 cells, without affecting $PGE_2$ production at the highest concentration tested (FIGS. 13B and C).

Formation of LG-Lysyl Adduct on Histone H4 Decreases DNA-Histone Interaction

To examine the functional effect of LG-histone adduction, we performed salt fractionation of A549 nuclei to determine histone solubility. In this assay, loosely-bound histone is released at lower salt concentrations than tightly-bound proteins. The present inventors discovered that in stimulated, AA-treated A549 cells, histone H4 was eluted at lower salt concentrations than in stimulated control cells; this was reversed after treatment with the scavenger EtSA (FIG. 14).

Discussion

As indicated herein, the present inventors established that COX-2 catalysis can cause changes in DNA-histone interactions through formation of LG-histone adducts, suggests a new hypothesis for the contribution of COX-2 to the etiology of cancer. Oxidative damage is known to cause $N^6$-formylation of H1 histone, and epigenetic modification affecting COX-2 transcription is well-described, but the LG-lysyl histone adduct we describe here is an entirely novel finding that links inflammation and COX-2 activation with histone modification.

The present inventors discovered COX-2 dependent formation of LG-histone adducts in cells and tissues. Whereas COX-2 blockade by treatment with indomethacin decreases LG-histone adduct formation in A549 or RAW264.7 cells, this method of antagonism cannot separate the myriad effects of other COX-2 products from the effects of the LG-histone adducts. The present inventors screened a number of small molecule levuglandin scavenger molecules for their ability to decrease LG-histone adduction. LG will react with these molecules three orders of magnitude faster than lysine, and we have previously shown that scavenger treatment decreases total cellular levels of LG-lysine adducts without affecting $PGE_2$ production. These scavengers are orally bioavailable, and able to decrease total LG-protein adduct levels when given to mice in drinking water. In future studies, aside from allowing investigation of LG-protein modification independent of COX activity, use of these scavengers may bypass the cardiovascular and gastric side effects seen with COX inhibitors.

Interestingly, not all histones are targeted, but cellular LG adducts seem to preferentially form on the H4 and, to a lesser extent, on H3/H2B. Whether this specificity is a reflection of histone availability in the nucleosome, accessibility of lysine residues, or a more favorable microenvironment for adduct formation remains to be shown. Incubation with $[^{14}C]$-AA in cells led to a stronger autoradiographic band at H3/H2B compared to H4, while LC-MS analysis indicated that H4 was the major form adducted by LGs. This discrepancy can be explained by several mechanisms. Protein-associated radioactivity would come from any product derived from $[^{14}C]$ AA, including LGs but also $PGJ_2/PGA_2$ cyclopentenone or arachidonate ester adducts. In addition, the occurrence of LG-lysyl adducts is almost certainly underreported with our current approach. Our internal standard and mass spectroscopy method are specific for detection of a single LG-lysyl adduct with an m/z equivalent to the lactam structure, but the initial Schiff base intermediate of LG-lysyl adducts can oxidize to form other structure such as hydroxylactam or intraprotein or protein-DNA crosslinks, which would go undetected in our method. For these reasons, the autoradiograms can not be quantitatively compared with the LC/EST/MS/MS results as they do not measure the same molecular structures.

H4, along with H2A, H2B, and H3 histones, comprise the histone octamer around which DNA is "packaged" into nucleosomes. The interaction of histone N-terminal tails with DNA is critical to DNA compaction and organization, and is dependent on the numerous positively charged lysine and arginine residues present; a mesoscopic model demonstrates that H4 tails are the most important in mediating internucleosomal interactions. A single lysyl acetylation on K16 of H4 modulates chromatin compaction and interaction of numerous chromatin-associated proteins; constitutive acetylation of this residue confers a folding defect comparable to deletion of the entire H4 tail. After LG-histone adduct formation we do find disruption of histone-DNA binding, resulting in increased DNA extraction in a salt solution. This decreased histone-DNA interaction may increase DNA transcriptional access to previously silent oncogenes, and contribute to the development of cancer.

The complex patterns of lysyl acetylation and methylation comprise a "histone code" that regulates chromatin access and transcription; it is plausible that irreversible adduction of lysyl residues could disrupt this code, or directly alter the access of DNA-interacting proteins. Changes in histone modifications are known to result in altered DNA methylation, deregulation of oncogenes, genomic instability, impaired DNA repair, and defects in cell cycle checkpoints. Changes in lysyl modifications of H4 in particular are a common hallmark of human cancers, and are associated with a global loss of DNA methylation. Further elucidation of the effects of LG-histone adduction on histone modification, DNA-histone interactions, and transcription should increase our understanding of the molecular mechanisms whereby COX-2 contributes to cancer development and progression.

Example 9. Inhibition of Formation of Levuglandin Adducts in an In Vivo Animal Model in which Intramucosal Gastric Carcinoma Develops Following Infection with *H. pylori*

To demonstrate that bifunctional electrophiles are generated in vivo during carcinogenesis, the present inventors analyzed the concentration of lysyl-Levuglandin (lysyl-LG) adducts using liquid chromatography electrospray ionization tandem mass spectrometry (LC/EST/MS/MS), in the whole gastric tissues of C57BL/6 mice (see FIG. 15A) and INS-GAS mice (FIG. 15B) infected by *H. pylori*. In both types of mice, lysyl-LG adduct levels were significantly increased in infected mice compared to uninfected animals, demonstrating that electrophiles are locally generated during the infection. To further determine whether ethylsalicylamine (EtSA) prevents the formation of bifunctional electrophiles during *H. pylori* infection, the mice were treated or not with EtSA 30 min prior to the infection. Our results show that lysyl-LG adduct concentration was significantly increased in *H. pylori*-infected AGS cells when compared to uninfected cells and completely attenuated by 10 µM EtSA (FIG. 15C).

Figures 16A, 16B, 16C, 16D, 16E, 16F:
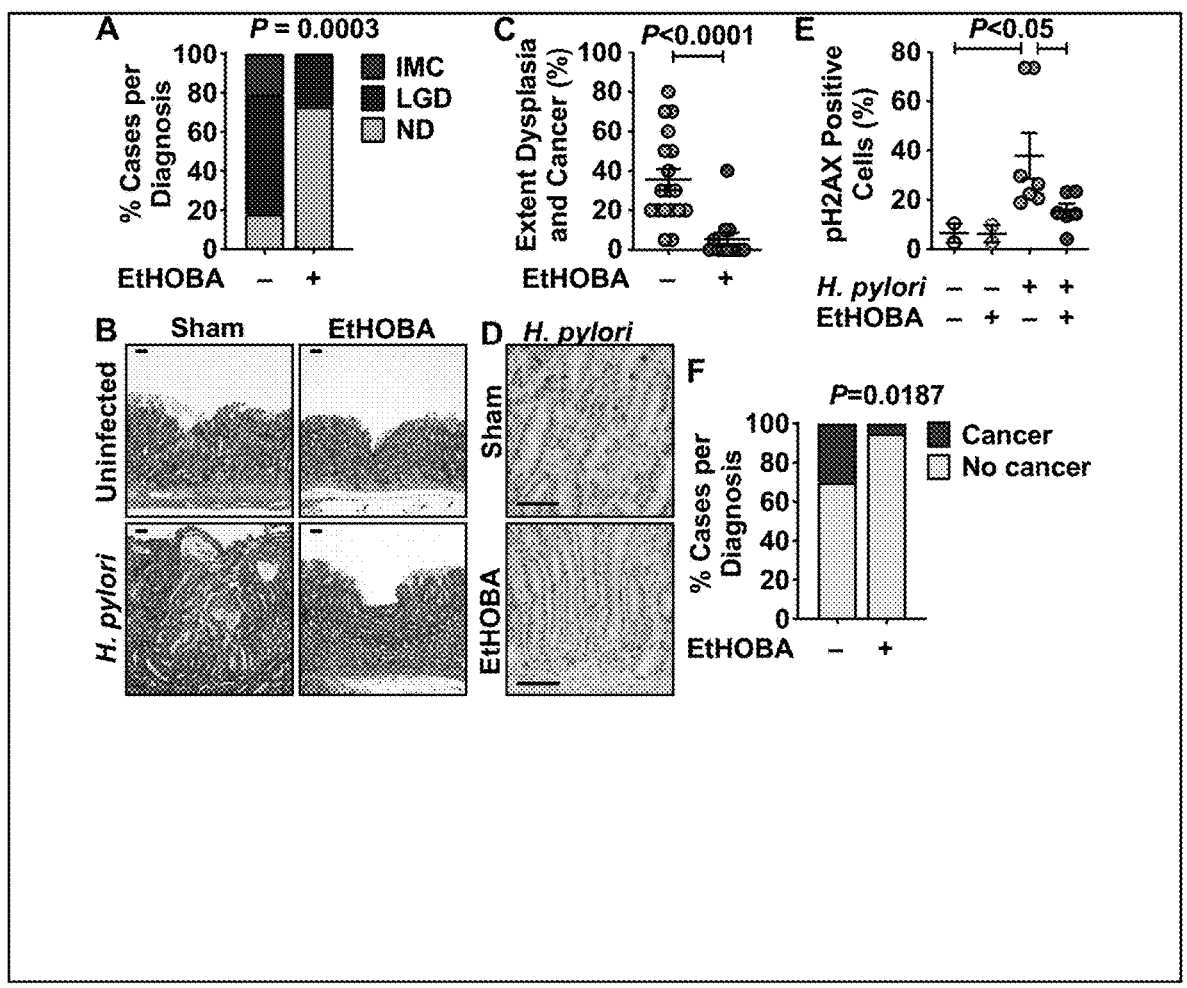

The effect of a scavenger of levuglandins and other dicarbonyls was investigated in transgenic INS-GAS mice, which have high circulating gastrin levels and develop atrophic gastritis, and dysplasia and carcinoma with *H. pylori* infection. Mice were infected with *H. pylori*, and then EtSA was administered in drinking water, starting 7 days after infection. After 8 weeks, EtSA levels were measured in the gastric tissues of uninfected and infected mice receiving this compound (FIG. 16A). There were significant decreases in development of dysplasia (from 37.5% to 14.3%) and carcinoma (from 37.5% to 0%) in *H. pylori*-infected INS-GAS mice treated with EtSA (FIG. 16B). Extent of dysplasia and carcinoma as a percentage of the gastric mucosa was also significantly attenuated by EtSA (FIG. 16C). FIG. 16D depicts hematoxylin and eosin (H&E) staining of the gastric mucosa of infected INS-GAS mice showing intramucosal carcinoma in an infected mouse, characterized by irregular and angulated glands with infiltration of the lamina propria by tumor cells and desmoplastic stroma; in contrast, infected mice treated with EtSA showed low grade dysplasia characterized by irregular proliferation of glands that do not infiltrate the stroma. There was no dysplasia or carcinoma in uninfected mice (FIG. 16D). It should be noted that gastric colonization by *H. pylori* was not reduced by EtSA treatment (data not shown), demonstrating that the protective effect of EtSA was unlikely due to an effect of EtSA on bacterial killing.

In summary, it is well established that in humans, *H. pylori* infection initiates an inflammatory process that leads to gastric cancer. The results of these investigations show that compounds of the present invention are useful for preventing the development of *H. pylori*-induced gastric cancer in humans.

REFERENCES

The following references are incorporated herein by reference in their entirety:
1. Agrawal, A., and Fentiman, I. S. (2008) NSAIDs and breast cancer: a possible prevention and treatment strategy, Int J Clin Pract 62, 444-449.
2. Harris, R. E., Beebe-Donk, J., and Alshafie, G. A. (2007) Reduced risk of human lung cancer by selective cyclooxygenase 2 blockade: results of a case control study, Int J Biol Sci 3, 328-334.
3. Konturek, P. C., Kania, J., Burnat, G., Hahn, E. G., and Konturek, S. J. (2005) Prostaglandins as mediators of COX-2 derived carcinogenesis in gastrointestinal tract, J Physiol Pharmacol 56 Suppl 5, 57-73.
4. Harris, R. E. (2009) Cyclooxygenase-2 (cox-2) blockade in the chemoprevention of cancers of the colon, breast, prostate, and lung, Inflammopharmacology 17, 55-67.
5. Lim, B. J., Jung, S. S., Choi, S. Y., and Lee, C. S. (2010) Expression of metastasis-associated molecules in non-small cell lung cancer and their prognostic significance, Mol Med Report 3, 43-49.
6. Sheehan, K. M., Sheahan, K., O'Donoghue, D. P., MacSweeney, F., Conroy, R. M., Fitzgerald, D. J., and Murray, F. E. (1999) The relationship between cyclooxygenase-2 expression and colorectal cancer, JAMA 282, 1254-1257.
7. Bertagnolli, M. M. (2007) Chemoprevention of colorectal cancer with cyclooxygenase-2 inhibitors: two steps forward, one step back, Lancet Oncol 8, 439-443.
8. Castellone, M. D., Teramoto, H., Williams, B. O., Druey, K. M., and Gutkind, J. S. (2005) Prostaglandin E2 promotes colon cancer cell growth through a Gs-axin-beta-catenin signaling axis, Science 310, 1504-1510.
9. Nakanishi, M., Montrose, D. C., Clark, P., Nambiar, P. R., Belinsky, G. S., Claffey, K. P., Xu, D., and Rosenberg, D. W. (2008) Genetic deletion of mPGES-1 suppresses intestinal tumorigenesis, Cancer research 68, 3251-3259.
10. Elander, N., Ungerback, J., Olsson, H., Uematsu, S., Akira, S., and Soderkvist, P. (2008) Genetic deletion of mPGES-1 accelerates intestinal tumorigenesis in APC Min/+ mice, Biochemical and biophysical research communications 372, 249-253.
11. Boutaud, O., Brame, C. J., Salomon, R. G., Roberts, L. J., 2nd, and Oates, J. A. (1999) Characterization of the lysyl adducts formed from prostaglandin H2 via the levuglandin pathway, Biochemistry 38, 9389-9396.
12. Salomon, R. G., Miller, D. B., Zagorski, M. G., and Coughlin, D. J. (1984) Solvent-induced fragmentation of prostaglandin endoperoxides. New aldehyde products from $PGH_2$ and a novel intramolecular 1,2-hydride shift during endoperoxide fragmentation in aqueous solution, J Am Chem Soc 106, 6049-6060.
13. Zagol-Ikapitte, I., Bernoud-Hubac, N., Amarnath, V., Roberts, L. J., 2nd, Boutaud, O., and Oates, J. A. (2004) Characterization of bis(levuglandinyl) urea derivatives as products of the reaction between prostaglandin H2 and arginine, Biochemistry 43, 5503-5510.
14. Boutaud, O., Brame, C. J., Chaurand, P., Li, J., Rowlinson, S. W., Crews, B. C., Ji, C., Marnett, L. J., Caprioli, R. M., Roberts, L. J., 2nd, and Oates, J. A. (2001) Characterization of the lysyl adducts of prostaglandin H-synthases that are derived from oxygenation of arachidonic acid, Biochemistry 40, 6948-6955.
15. Iyer, R. S., Ghosh, S., and Salomon, R. G. (1989) Levuglandin E2 crosslinks proteins, Prostaglandins 37, 471-480.
16. Boutaud, O., Li, J., Zagol, I., Shipp, E. A., Davies, S. S., Roberts, L. J., 2nd, and Oates, J. A. (2003) Levuglandinyl adducts of proteins are formed via a prostaglandin H2 synthase-dependent pathway after platelet activation, The Journal of biological chemistry 278, 16926-16928.
17. Boutaud, O., Andreasson, K. I., Zagol-Ikapitte, I., and Oates, J. A. (2005) Cyclooxygenase-dependent lipid-modification of brain proteins, Brain Pathol 15, 139-142.
18. Jenuwein, T., and Allis, C. D. (2001) Translating the histone code, Science 293, 1074-1080.
19. Esteller, M. (2007) Cancer epigenomics: DNA methylomes and histone-modification maps, Nat Rev Genet 8, 286-298.
20. Fraga, M. F., Ballestar, E., Villar-Garea, A., Boix-Chornet, M., Espada, J., Schotta, G., Bonaldi, T., Haydon, C., Ropero, S., Petrie, K., Iyer, N. G., Perez-Rosado, A., Calvo, E., Lopez, J. A., Cano, A., Calasanz, M. J., Colomer, D., Piris, M. A., Ahn, N., Imhof, A., Caldas, C., Jenuwein, T., and Esteller, M. (2005) Loss of acetylation at Lys16 and trimethylation at Lys20 of histone H4 is a common hallmark of human cancer, Nat Genet 37, 391-400.
21. Zagol-Ikapitte, I., Amarnath, V., Bala, M., Roberts, L. J., 2nd, Oates, J. A., and Boutaud, O. (2010) Characterization of scavengers of gamma-ketoaldehydes that do not inhibit prostaglandin biosynthesis, Chemical research in toxicology 23, 240-250.
22. Zagol-Ikapitte, I., Masterson, T. S., Amarnath, V., Montine, T. J., Andreasson, K. I., Boutaud, O., and Oates, J. A. (2005) Prostaglandin H(2)-derived adducts of proteins correlate with Alzheimer's disease severity, Journal of neurochemistry 94, 1140-1145.
23. Shechter, D., Dormann, H. L., Allis, C. D., and Hake, S. B. (2007) Extraction, purification and analysis of histones, Nat Prot 2, 1445-1457.
24. Bhaskara, S., Knutson, S. K., Jiang, G., Chandrasekharan, M. B., Wilson, A. J., Zheng, S., Yenamandra, A., Locke, K., Yuan, J.-L., Bonine-Summers, A. R., Wells, C. E., Kaiser, J. F., Washington, M. K., Zhao, Z., Wagner, F. F., Sun, Z.-W., Xia, F., Holson, E. B., Khabele, D., and Hiebert, S. W. (2010) Hdac3 is essential for the maintenance of chromatin structure and genome stability, Cancer Cell 18, 436-447.
25. Sanders, M. M. (1978) Fractionation of nucleosomes by salt elution from micrococcal nuclease-digested nuclei, J Cell Biol 79, 97-109.
26. Jiang, T., Zhou, X., Taghizadeh, K., Dong, M., and Dedon, P. C. (2007) N-formylation of lysine in histone proteins as a secondary modification arising from oxidative DNA damage, Proceedings of the National Academy of Sciences of the United States of America 104, 60-65.
27. Fernandez-Alvarez, A., Llorente-Izquierdo, C., Mayoral, R., Agra, N., Bosca, L., Casado, M., and Martin-Sanz, P. (2012) Evaluation of epigenetic modulation of cyclooxygenase-2 as a prognostic marker for hepatocellular carcinoma, Oncogenesis 1, e23.
28. Amarnath, V., Amarnath, K., Davies, S., and Roberts, L. J. n. (2004) Pyridoxamine: an extremely potent scavenger of 1,4-dicarbonyls, Chemical research in toxicology 17, 410-415.
29. Zagol-Ikapitte, I., Amarnath, V., Jadhav, S., Oates, J. A., and Boutaud, 0. (2011) Determination of 3-methoxysalicylamine levels in mouse plasma and tissue by liquid chromatography-tandem mass spectrometry: application to in vivo pharmacokinetics studies, Journal of chromatography 879, 1098-1104.
30. Zagol-Ikapitte, I. A., Matafonova, E., Amarnath, V., Bodine, C. L., Boutaud, O., Tirona, R. G., Oates, J. A., Roberts, L. J., 2nd, and Davies, S. S. (2010) Determination of the pharmacokinetics and oral bioavailability of salicylamine, a potent gamma-ketoaldehyde scavenger, by LC/MS/MS, Pharmaceutics 2, 18-29.
31. Murthi, K. K., Friedman, L. R., Oleinick, N. L., and Salomon, R. G. (1993) Formation of DNA-protein cross-links in mammalian cells by levuglandin E2, Biochemistry 32, 4090-4097.
32. Arya, G., and Schlick, T. (2006) Role of histone tails in chromatin folding revealed by a mesoscopic oligonucleosome model, Proceedings of the National Academy of Sciences of the United States of America 103, 16236-16241.
33. Shogren-Knaak, M., Ishii, H., Sun, J.-M., Pazin, M. J., Davie, J. R., and Peterson, C. L. (2006) Histone H4-K16 acetylation controls chromatin structure and protein interactions, Science 311, 844-847.
34. Fuks, F. (2005) DNA methylation and histone modifications: teaming up to silence genes, Curr Opin Genet Dev 15, 490-495.
35. Füllgrabe, J., Kavanagh, E., and Joseph, B. (2011) Histone onco-modifications, Oncogene 30, 3391-3403.
36. Carrier, E. J., et al., Characterization of covalent adducts of nucleosides and DNA formed by reaction with levuglandin. Biochemistry, 2009. 48(45): p. 10775-81.
37. Wang, T. C., et al., Synergistic interaction between hypergastrinemia and *Helicobacter* infection in a mouse model of gastric cancer. Gastroenterology, 2000. 118(1): p. 36-47.
38. Sierra, J. C., et al., Epidermal growth factor receptor inhibition downregulates *Helicobacter pylori*-induced epithelial inflammatory responses, DNA damage and gastric carcinogenesis. Gut, 2017.

39. Chaturvedi, R., et al., Activation of EGFR and ERBB2 by *Helicobacter pylori* results in survival of gastric epithelial cells with DNA damage. Gastroenterology, 2014. 146(7): p. 1739-51 e14.

It will be understood that various details of the presently disclosed subject matter can be changed without departing from the scope of the subject matter disclosed herein. Furthermore, the foregoing description is for the purpose of illustration only, and not for the purpose of limitation.

We claim:

1. A method of inhibiting the progression of a gastrointestinal cancer induced by a *Helicobacter pylori* infection immune response in a subject, comprising administering to the subject a levuglandin adduct formation inhibiting amount of a compound of the following formula:

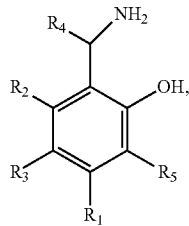

wherein:
$R_1$ is H, D, $D_2$, substituted or unsubstituted alkyl, substituted or unsubstituted alkoxy, carboxyl, substituted or unsubstituted aryl, or substituted or unsubstituted cycloalkyl;
$R_2$ is H, substituted or unsubstituted alkyl, substituted or unsubstituted alkoxy, alkyl-alkoxy-$R_4$;
$R_3$ is H, halogen, substituted or unsubstituted alkyl, substituted or unsubstituted alkoxy, hydroxyl, nitro;
$R_4$ is H, D, $D_2$, substituted or unsubstituted alkyl, substituted or unsubstituted alkoxy, carboxyl, substituted or unsubstituted aryl, or substituted or unsubstituted cycloalkyl;
$R_5$ is H, substituted or unsubstituted alkyl, substituted or unsubstituted alkoxy; and pharmaceutical salts thereof.

2. The method of claim 1, wherein the cancer is colorectal cancer.

3. The method of claim 1, wherein $R_1$ is $CH_3$ or alkyl.

4. The method of claim 1, wherein one of $R_2$, $R_3$, or $R_5$ is $CH_3$ or alkyl.

5. The method of claim 1, wherein the compound is of the following formula:

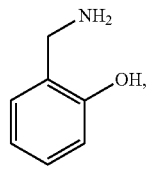

and pharmaceutical salts thereof.

6. The method of claim 1, wherein the compound is 2-hydroxybenzylamine, methyl-2-hydroxybenzylamine, or ethyl-2-hydroxybenzylamine.

7. The method of claim 1, wherein the subject is diagnosed with a *H. pylori* infection prior to the administration step.

8. A method of mitigating the progression of pre-malignant lesions induced by a *Helicobacter pylori* infection immune response in a subject in need thereof by administering an effective amount of a compound of the following formula:

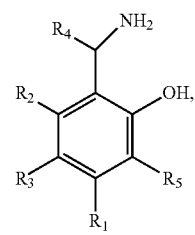

wherein:
$R_1$ is H, D, $D_2$, substituted or unsubstituted alkyl, substituted or unsubstituted alkoxy, carboxyl, substituted or unsubstituted aryl, or substituted or unsubstituted cycloalkyl;
$R_2$ is H, substituted or unsubstituted alkyl, substituted or unsubstituted alkoxy, alkyl-alkoxy-$R_4$;
$R_3$ is H, halogen, substituted or unsubstituted alkyl, substituted or unsubstituted alkoxy, hydroxyl, nitro;
$R_4$ is H, D, $D_2$, substituted or unsubstituted alkyl, substituted or unsubstituted alkoxy, carboxyl, substituted or unsubstituted aryl, or substituted or unsubstituted cycloalkyl;
$R_5$ is H, substituted or unsubstituted alkyl, substituted or unsubstituted alkoxy; and pharmaceutical salts thereof.

9. The method of claim 8, wherein the lesions are in a gastrointestinal tract.

10. The method of claim 8, wherein $R_1$ is $CH_3$ or alkyl.

11. The method of claim 8, wherein one of $R_2$, $R_3$, or $R_5$ is $CH_3$ or alkyl.

12. The method of claim 8, wherein the compound is of the following formula:

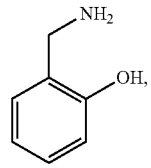

and pharmaceutical salts thereof.

13. The method of claim 8, wherein the compound is 2-hydroxybenzylamine, methyl-2-hydroxybenzylamine, or ethyl-2-hydroxybenzylamine.

14. A method of treating or inhibiting the progression of gastrointestinal carcinoma in a subject in need thereof, comprising administering an effective *H. pylori* infection reducing amount of a compound of the following formula:

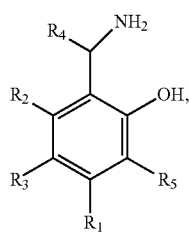

wherein:
R₁ is H, D, D₂, substituted or unsubstituted alkyl, substituted or unsubstituted alkoxy, carboxyl, substituted or unsubstituted aryl, or substituted or unsubstituted cycloalkyl;
R₂ is H, substituted or unsubstituted alkyl, substituted or unsubstituted alkoxy, alkyl-alkoxy-R₄;
R₃ is H, halogen, substituted or unsubstituted alkyl, substituted or unsubstituted alkoxy, hydroxyl, nitro;
R₄ is H, D, D₂, substituted or unsubstituted alkyl, substituted or unsubstituted alkoxy, carboxyl, substituted or unsubstituted aryl, or substituted or unsubstituted cycloalkyl;
R₅ is H, substituted or unsubstituted alkyl, substituted or unsubstituted alkoxy; and pharmaceutical salts thereof.

15. The method of claim 14, wherein the compound is of the following formula:

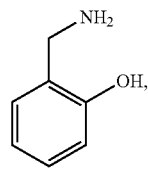

and pharmaceutical salts thereof.

16. The method of claim 14, wherein the compound is 2-hydroxybenzylamine, methyl-2-hydroxybenzylamine, or ethyl-2-hydroxybenzylamine.

17. The method of claim 14, further including the step of, prior to the administration step, diagnosing the subject as being infected with *H. pylori* in the gastrointestinal tract.

18. The method of claim 8, wherein the lesion exists in the colon, esophagus, breast, lung, pancreas, gastrointestinal tract, and/or prostate.

19. The method of claim 1, wherein said inhibition lowers levels of LG-histone adduct formation in said subject.

* * * * *

UNITED STATES PATENT AND TRADEMARK OFFICE
CERTIFICATE OF CORRECTION

| | |
|---|---|
| PATENT NO. | : 11,696,903 B2 |
| APPLICATION NO. | : 16/893425 |
| DATED | : July 11, 2023 |
| INVENTOR(S) | : Wilson et al. |

It is certified that error appears in the above-identified patent and that said Letters Patent is hereby corrected as shown below:

In the Specification

Column 1, Line 12 Replace the second paragraph, with the following:
Government Interest
This invention was made with government support under Grant Nos. ES000267, CA090949, CA201856, CA028842, CA116087, CA190612, CA187495, DK053620, DK058404, DK007383 and GM015431 awarded by the National Institutes of Health and Grant No. W81XWH-18-1-030, awarded by the Department of the Army. The government has certain rights in the invention.

Signed and Sealed this
Seventeenth Day of September, 2024

Katherine Kelly Vidal
*Director of the United States Patent and Trademark Office*